(12) United States Patent
Carrara et al.

(10) Patent No.: US 7,198,801 B2
(45) Date of Patent: *Apr. 3, 2007

(54) FORMULATIONS FOR TRANSDERMAL OR TRANSMUCOSAL APPLICATION

(75) Inventors: Dario Norberto R. Carrara, Oberwil (CH); Arnaud Grenier, Steinbrunn le Haut (FR); Celine Besse, Saint Louis (FR); Stephen M. Simes, Long Grove, IL (US); Leah M. Lehman, Green Oaks, IL (US)

(73) Assignee: Antares Pharma IPL AG, Zug (CH)

( * ) Notice: Subject to any disclaimer, the term of this patent is extended or adjusted under 35 U.S.C. 154(b) by 326 days.

This patent is subject to a terminal disclaimer.

(21) Appl. No.: 10/798,161

(22) Filed: Mar. 10, 2004

(65) Prior Publication Data

US 2004/0219197 A1 Nov. 4, 2004

Related U.S. Application Data

(63) Continuation-in-part of application No. 10/343,570, filed as application No. PCT/EP01/09007 on Aug. 3, 2001, said application No. 10/798,161.

(60) Provisional application No. 60/510,613, filed on Oct. 10, 2003, provisional application No. 60/453,604, filed on Mar. 11, 2003.

(30) Foreign Application Priority Data

Aug. 3, 2000 (EP) .................... PCT/EP00/07533

(51) Int. Cl.
*A61F 13/00* (2006.01)
*A61K 9/70* (2006.01)
*A61K 31/56* (2006.01)
*A01N 45/00* (2006.01)

(52) U.S. Cl. ...................... 424/449; 514/169

(58) Field of Classification Search ................ 424/448, 424/449; 514/169
See application file for complete search history.

(56) References Cited

U.S. PATENT DOCUMENTS

| | | | |
|---|---|---|---|
| 4,082,881 A | 4/1978 | Chen et al. | 424/241 |
| 4,315,925 A | 2/1982 | Hussaiin et al. | 424/239 |
| 4,383,993 A | 5/1983 | Hussaiin et al. | 424/239 |
| 4,390,532 A | 6/1983 | Stuttgen et al. | 424/240 |
| 4,537,776 A | 8/1985 | Cooper | 514/424 |
| 4,863,970 A | 9/1989 | Patel et al. | 514/784 |
| 4,952,560 A | 8/1990 | Kigasawa et al. | 514/2 |
| 5,071,657 A | 12/1991 | Oloff et al. | 424/486 |
| 5,128,138 A | 7/1992 | Blank | 424/449 |
| 5,178,879 A | 1/1993 | Adekunle et al. | 424/484 |
| 5,232,703 A | 8/1993 | Blank | 424/449 |
| 5,238,933 A | 8/1993 | Catz et al. | 514/236.2 |

(Continued)

FOREIGN PATENT DOCUMENTS

EP 0 249 397 12/1987

(Continued)

OTHER PUBLICATIONS

US 6,214,374, 04/2001, Schmirier et al. (withdrawn)

*Primary Examiner*—Sreeni Padmanabhan
*Assistant Examiner*—Konata M. George
(74) *Attorney, Agent, or Firm*—Winston & Strawn LLP

(57) ABSTRACT

The present invention relates generally to formulations for transdermal or transmucosal administration of an active agent. The invention is a substantially malodorous-free and irritation free transdermal formulation which is substantially free of long chain fatty alcohols, long-chain fatty acids, and long-chain fatty esters.

28 Claims, 11 Drawing Sheets

U.S. PATENT DOCUMENTS

| | | | |
|---|---|---|---|
| 5,371,005 A | 12/1994 | Fujishiro et al. | 435/190 |
| 5,580,574 A | 12/1996 | Behl et al. | 424/449 |
| 5,602,017 A | 2/1997 | Fujishiro et al. | 435/190 |
| 5,629,021 A | 5/1997 | Wright | 424/489 |
| 5,660,839 A | 8/1997 | Allec et al. | 424/401 |
| 5,665,560 A | 9/1997 | Fujishiro et al. | 435/11 |
| 5,716,638 A | 2/1998 | Touitou | 424/450 |
| 5,731,303 A | 3/1998 | Hsieh | 514/183 |
| 5,798,242 A | 8/1998 | Fujishiro et al. | 435/190 |
| 5,831,035 A | 11/1998 | Timms | 530/389.1 |
| 5,855,905 A | 1/1999 | Oettel et al. | 424/426 |
| 5,855,920 A | 1/1999 | Chein | 424/568 |
| 5,891,462 A | 4/1999 | Carrara | 424/449 |
| 5,904,931 A | 5/1999 | Lipp et al. | 424/449 |
| 5,968,919 A | 10/1999 | Samour et al. | 514/177 |
| 6,008,192 A | 12/1999 | Al-Razzak et al. | 514/11 |
| 6,060,077 A | 5/2000 | Meignant | 424/434 |
| 6,096,733 A | 8/2000 | Lubkin | 514/182 |
| 6,153,216 A | 11/2000 | Cordes | 424/449 |
| 6,180,803 B1 | 1/2001 | Piasco et al. | 552/150 |
| 6,284,234 B1 | 9/2001 | Niemiec | 424/78.07 |
| 6,299,900 B1 | 10/2001 | Reed et al. | 424/449 |
| 6,309,843 B1 | 10/2001 | Timms | 435/7.1 |
| 6,319,913 B1 | 11/2001 | Mak et al. | 514/179 |
| 6,440,454 B1 | 8/2002 | Santoro et al. | 424/449 |
| 6,444,234 B1 | 9/2002 | Kirby et al. | 424/725 |
| 6,476,012 B2 | 11/2002 | Hochberg | 514/182 |
| 6,497,897 B2 | 12/2002 | Hidaka et al. | 424/449 |
| 6,503,894 B1 | 1/2003 | Dudley | 514/178 |
| 6,586,000 B2 | 7/2003 | Luo et al. | 424/449 |
| 6,818,226 B2 | 11/2004 | Reed et al. | 424/449 |
| 6,923,983 B2 | 8/2005 | Morgan et al. | 424/448 |
| 2001/0023261 A1 | 9/2001 | Ryoo | 514/772 |
| 2001/0033870 A1 | 10/2001 | Luo | 424/688 |
| 2002/0183296 A1 | 12/2002 | Dudley et al. | 514/177 |
| 2003/0022877 A1 | 1/2003 | Dudley | 514/177 |
| 2003/0050292 A1 | 3/2003 | Dudley | 514/177 |
| 2003/0139384 A1 | 7/2003 | Dudley | 514/177 |
| 2003/0181430 A1 | 9/2003 | Gray et al. | 514/170 |
| 2003/0232072 A1 | 12/2003 | Dudley et al. | 424/449 |
| 2004/0002482 A1 | 1/2004 | Dudley et al. | 514/169 |
| 2004/0198706 A1* | 10/2004 | Carrara et al. | 514/169 |
| 2005/0142175 A1 | 6/2005 | Langguth et al. | 424/449 |

FOREIGN PATENT DOCUMENTS

| | | |
|---|---|---|
| EP | 0250125 B1 | 9/1991 |
| EP | 0325613 B1 | 9/1993 |
| EP | 0 672 422 A1 | 3/1994 |
| EP | 0409383 B1 | 4/1994 |
| EP | 0435200 B1 | 7/1995 |
| EP | 785211 A1 | 7/1997 |
| EP | 785212 A1 | 7/1997 |
| EP | 0 811 381 A1 | 12/1997 |
| EP | 0491803 B1 | 7/1999 |
| EP | 0804926 B1 | 10/1999 |
| EP | 0655900 B1 | 3/2000 |
| EP | 0719538 B1 | 11/2000 |
| EP | 0814776 B1 | 7/2001 |
| EP | 0643963 B1 | 11/2001 |
| EP | 0868187 B1 | 12/2001 |
| EP | 0859793 B1 | 2/2002 |
| EP | 1089722 B1 | 5/2002 |
| EP | 0802782 B1 | 2/2003 |
| FR | 2518879 | 12/1981 |
| FR | 2776191 | 9/1999 |
| JP | 09176049 | 7/1997 |
| WO | WO 92/08730 | 5/1992 |
| WO | WO 94/06437 | 3/1994 |
| WO | WO 97/03676 | 2/1997 |
| WO | WO 97/34607 | 9/1997 |
| WO | WO 98/37879 | 9/1998 |
| WO | WO 99/24041 | 5/1999 |
| WO | WO 99/48477 | 9/1999 |
| WO | WO 99/20257 | 4/2001 |
| WO | WO 02/22132 | 2/2002 |

* cited by examiner

FORMULATIONS FOR TRANSDERMAL OR TRANSMUCOSAL APPLICATION

CROSS REFERENCE TO RELATED APPLICATIONS

This application is a continuation-in-part of U.S. patent application Ser. No. 10/343,570 filed May 19, 2003, which is the US national stage of International Application PCT/EP01/09007 filed Aug. 3, 2001, and claims priority to U.S. Provisional Patent Applications 60/510,613 filed Oct. 10, 2003 and 60/453,604 filed Mar. 11, 2003. Each prior application is expressly incorporated herein in its entirety by reference thereto.

BACKGROUND OF THE INVENTION

1. Field of Invention

The present invention relates generally to formulations for the transdermal or transmucosal delivery of active agents. In particular, the present invention is directed to a substantially malodorous-free and irritation-free transdermal formulation which is substantially free of long chain fatty alcohols, long chain fatty acids, and long-chain fatty esters, and which delivers effective therapeutic levels of an active agent.

2. Background Art

Transdermal and/or transmucosal delivery of active agents provide a convenient, pain-free, and non-invasive method of administering active agents to a subject. Additionally, the administration of active agents, such as drugs, through the skin or mucosal surface avoids the well-documented problems associated with the "first pass effect" encountered by oral administration of active agents. As known in the art, orally administered drugs are absorbed and enter the bloodstream where they are transported by the portal vein directly to the liver before entering the general circulation of the body. If the drug is subject to a high hepatic clearance, i.e., it is rapidly metabolized by the liver, then a substantial fraction of the absorbed dose is extracted from the blood and metabolized before it ever reaches the systemic circulation. The consequence of this "first pass effect" phenomenon is a significant reduction in the bioavailability of the drug. In some instances, the first pass effect is so large as to render oral administration of a drug ineffective.

Although the transdermal and/or transmucosal delivery of active agents overcome some of the problems associated with oral administration of active agents, such as that described above, they are not free of their own drawbacks. Problematically, transdermal drug delivery systems are typically restricted to low-molecular weight drugs and those with structures having the proper lipophilic/hydrophilic balance. High molecular weight drugs, or drugs with too high or low hydrophilic balance, often cannot be incorporated into current transdermal systems in concentrations high enough to overcome their impermeability through the stratum corneum. Specifically, polar drugs tend to penetrate the skin too slowly, and since most drugs are of a polar nature, this limitation is significant.

Efforts have been made in the art to chemically modify the barrier properties of skin to permit the penetration of certain agents (since diffusion is primarily controlled through the stratum corneum), enhance the effectiveness of the agent being delivered, enhance delivery times, reduce the dosages delivered, reduce the side effects from various delivery methods, reduce patient reactions, and so forth.

In this regard, penetration enhancers have been used to increase the permeability of the dermal surface to drugs, and are often protons accepting solvents such as dimethyl sulfoxide (DMSO) and dimethylacetamide. Other penetration enhancers that have been studied and reported as effective include 2-pyrrolidine, N,N-diethyl-m-toluamide (Deet), 1-dodecal-azacycloheptane-2-one N,N-dimethylformamide, N-methyl-2-pyrrolidine, calcium thioglycolate, hexanol, fatty acids and esters, pyrrolidone derivatives, derivatives of 1,3-dioxanes and 1,3-dioxolanes, 1-N-dodecyl-2-pyrrolidone-5-carboxylic acid, 2-pentyl-2-oxo-pyrrolidineacetic acid, 2-dodecyl-2-oxo-1-pyrrolidineacetic acid, 1-azacycloheptan-2-one-2-dodecylacetic acid, and aminoalcohol derivatives, including derivatives of 1,3-dioxanes, among others.

The most common penetration enhancers, however, are toxic, irritating, oily, odiferous, or allergenic. Specifically, the penetration enhancers used and thought to be necessary to transdermally deliver active agents such as steroid hormones, namely, compounds such as long chain fatty acids such as oleic acids, fatty alcohols such as lauryl alcohol and long-chain fatty esters such as isopropyl myristate, tend to include aliphatic groups that make the formulations oily and malodorous.

For example, U.S. Pat. No. 5,891,462 teaches the use of lauryl alcohol as a permeation enhancer for estradiol and norethindrone acetate. Such formulations are not appealing to the user nor to anyone else in close proximity to the user. Although this particular patent discloses three examples of estradiol or norethindrone acetate formulations having no lauryl alcohol component, such formulations are comparative examples that are intended to illustrate the long held position that long chain fatty alcohols such as lauryl alcohol are necessary to transdermally deliver norethindrone acetate in combination with estradiol to a subject.

Additionally, for example, the known testosterone gel formulations FORTIGEL® and TOSTRELLE® (Cellegy Pharma, South San Francisco, Calif.), both include ethanol, propanol, propylene glycol, carbomer, triethanolamine, purified water, and oleic acid as a permeation enhancer, the latter being responsible for the irritating and malodorous characteristics of these formulations. Also, TESTIM® (Auxilium Pharmaceuticals, Norristown, Pa.) is a 1% testosterone gel and includes pentadecalactone, acrylates, glycerin, polyethylene glycol (PEG), and pentadecalactone as a permeation enhancer. It is a very odoriferous compound. Also, TESTIM® is not desirable because it contains undesirable amounts of glycerin which are not well tolerated by the skin.

Thus, there is a need for a transdermal formulation that adequately delivers active agents to patients with skin tolerability, but does not include the unpleasant odor common to the prior art formulations.

SUMMARY OF THE INVENTION

The present invention relates to transdermal or transmucosal malodorous-free and irritation-free formulations comprising an active agent and delivery vehicle. In particular, the formulation comprises at least one active agent; and a delivery vehicle, which may comprise a $C_2$ to $C_4$ alkanol, a polyalcohol, and a permeation enhancer of monoalkyl ether of diethylene glycol present in an amount sufficient to provide permeation enhancement of the active agent through mammalian dermal or mucosal surfaces. The formulation is substantially free of long-chain fatty alcohols, long chain fatty acids and long-chain fatty esters in order to avoid potential undesirable odor and irritation effects caused by such compounds during use of the formulation. Thus, advantageously, the formulations of the present invention do not include the undesirable-odor causing and irritation causing permeation enhancers that were once thought to be necessary for such transdermal or transmucosal formulations.

In accordance with the invention, the polyalcohol may be advantageously present in an amount between about 1% and 30% by weight of the vehicle. The monoalkyl ether of diethylene glycol may be present in an amount of about 0.2% and 25% by weight of the vehicle and the alkanol may be present in an amount between about 5 to 75% by weight of the vehicle. Generally, the alkanol can be present in a hydroalcoholic mixture with water.

The alkanol may be an ethanol, isopropanol, or n-propanol. Preferably, the alkanol is ethanol. The polyalcohol may be propylene glycol, butylene glycol, hexylene glycol, and ethylene glycol. Preferably, the polyalcohol is propylene glycol. The permeation enhancer of monoalkyl ether of diethylene is, for example, diethylene glycol monoethyl ether or diethylene glycol monomethyl ether. Preferably, the permeation enhancer is diethylene glycol monoethyl ether.

The active agent may be selected from androgens, estrogens, or progestogens or any combination thereof, for example, androgens plus estrogens, androgens plus progestogens, or androgens plus estrogens, plus progestogens, provided that when the active agent is an estrogen or a progestogen, a therapeutically effective amount of a progestogen or estrogen, respectively, is not present in the formulation. Particularly preferred active agents include: androgens, anti-androgens, estrogens, anti-estrogens, progestogens, anti-progestogens, adrenergic agonists, analgesics, sedatives, amides, arylpiperazines, nerve agents, antineoplastics, anti-inflammatory agents, anticholinergics, anticonvulsants, antidepressants, antiepileptics, antihistaminics, antihypertensives, muscle relaxants, diuretics, bronchodilators, and glucocorticoids. If desired, the active agent may be present in combination with a secondary active agent for concurrent administration subject to the previously stated provision.

The formulation can further include at least one of a gelling agent, neutralizing agent; buffering agent, moisturizing agent, humectant, surfactant, antioxidant, emollient, or buffer, and the like. The formulation may be applied in the form of a gel, lotion, cream, spray, aerosol, ointment, emulsion, suspension, liposomal system, lacquer, patch, bandage, or occlusive dressing and the like.

BRIEF DESCRIPTION OF THE DRAWINGS

The features and benefits of the invention will now become more clear from a review of the following detailed description of illustrative embodiments and the accompanying drawings, wherein.

DETAILED DESCRIPTION OF THE PREFERRED EMBODIMENTS

Figure 1:
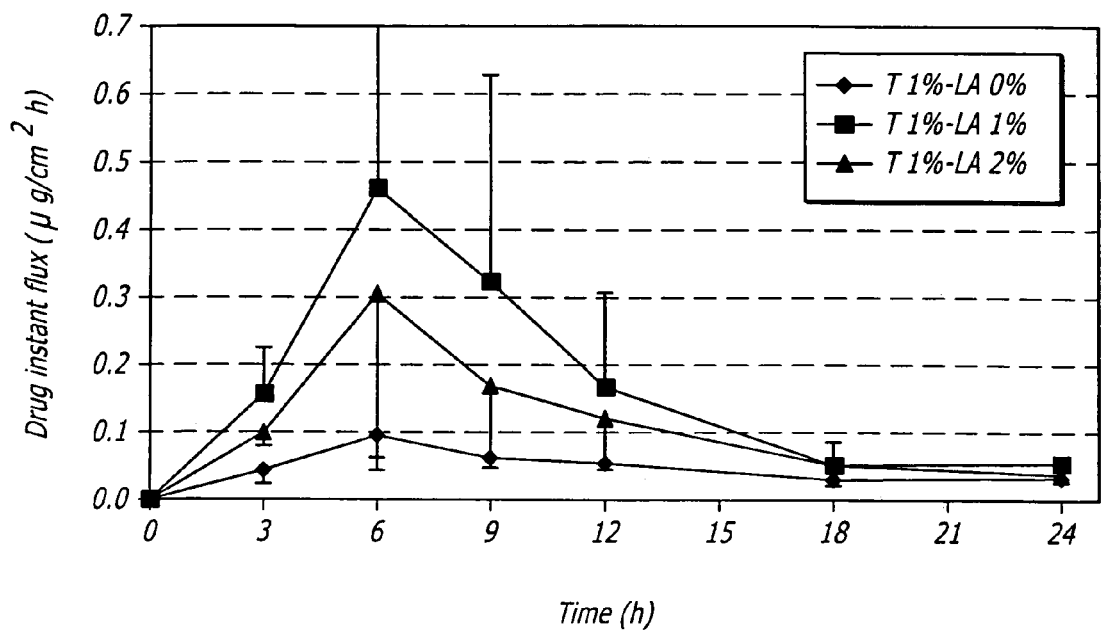
FIG. 1 is a graph depicting drug flux over time for testosterone in formulations including various amounts of lauryl alcohol (LA) in an in vitro model using human excised skin and 10 mg testosterone/cm$^2$ in the loading chamber (n=3–4±SD).

The formulations of the present invention may be clear, water washable, cool to the touch, quick drying, spreadable and/or a non-greasy formulations, such as a gel. In other aspects of the invention, the formulation may be a spray, ointment, aerosol, patch, buccal and sublingual tablets, suppositories, vaginal dosage form, or other passive or active transdermal devices for absorption through the skin or mucosal surface. The formulations of the present invention may be applied directly to the skin such as by, for example and not limitation, a gel, ointment, or cream or indirectly though a patch, bandage, or other occlusive dressing.

Advantageously, the substantial omission of the long chain fatty alcohols, long-chain fatty acids, and long-chain fatty esters provides a formulation that does not have the unpleasant odor, irritation, and/or greasy texture caused by formulations of the prior art that include one or more of such compounds. Thus, the formulation in accordance with the present invention will result in greater patient compliance. The inventive formulations are substantially free of such alcohols, fatty acids, and long-chain fatty esters so that the odors associated with those compounds do not emanate from the formulation. In this regard, "substantially free" means an amount which does not impart a perceptible odor to the formulation at a distance of 1 meter. Such formulations are also deemed to be substantially odor free. For the purpose of example and illustration, a formulation comprising fatty alcohols, fatty acids and/or fatty esters in an amount of less than about 0.04% by weight of the formulation is substantially odor free.

The present invention relates generally to formulations for providing active agents to subjects. The invention further relates to formulations for the transdermal or transmucosal administration of active agents that are substantially free of malodorous, and irritation causing long-chain fatty alcohols, long-chain fatty acids, and long-chain fatty esters. Surprisingly, the formulation of the present invention can achieve sufficient absorption to result in an effective dosage of the selected active agent(s) circulating in serum without the inclusion of the long-chain fatty alcohols, the long-chain fatty acids and the long-chain fatty esters that have been used to date.

The delivery vehicle of the present invention preferably comprises a $C_2$ to $C_4$ alkanol, a polyalcohol, and a permeation enhancer of monoalkyl ether of diethylene glycol in an amount sufficient to provide permeation enhancement of the active agent through mammalian dermal or mucosal surfaces.

In accordance with the invention, the polyalcohol is advantageously present in an amount between about 1% and 30% of the vehicle, preferably from 3% to 20% w/w and more preferably from about 4% to 10% w/w. The monoalkyl ether of diethylene glycol is present in an amount of about 0.2% and 25%, preferably between about 1% to 15% w/w and more preferably between about 2% to 8% w/w. The alkanol is present in an amount between about 5 to 75% w/w, preferably between about 15% to 65%, and more preferably between about 20% and 55% w/w. The alkanol can be present in a hydroalcoholic mixture with water. The mixture is present in an amount between about 40% and 98% of the delivery vehicle, with the alcohol being present in an amount between about 5% to 80% w/w of the hydroalcoholic mixture, and the water present in an amount between about 20% to 95% w/w of the hydroalcoholic mixture. Preferably, the alcohol is present in an amount of about 50 to 60% and the water in an amount of 50 to 40% of the hydroalcoholic mixture.

For example, the monoalkyl ether of diethylene glycol is diethylene glycol monomethyl ether or diethylene glycol monoethyl ether or mixtures thereof. Also for example, the polyalcohol is propylene glycol, dipropylene glycol or mixtures thereof. The polyalcohol and the permeation enhancer may be in present in a weight ratio of about 2:1 to 1:1. Alternatively, the polyalcohol and permeation enhancer may be present in a weight ratio of about 1.25:1 to 1.2 to 1.

For the purpose of illustration and not limitation, the alkanol may be a C2 to C4 alcohol such as ethanol, isopropanol, or n-propanol. The alkanol is preferably ethanol. As known in the art, the amount of the alcoholic component of the formulation may be selected to maximize the diffusion of the active agent through the skin while minimizing any negative impact on the active agent itself or desirable properties of the formulation.

The formulations of the invention may include at least one or a combination of active agents. The "active agent" is used herein to refer to a substance or formulation or combination of substances or formulations of matter which, when administered to an organism (human or animal) induces a desired pharmacologic and/or physiologic effect by local and/or systemic action.

The active agent of the formulation may be selected from the group including: androgens, anti-androgens, estrogens, anti-estrogens, progestogens, anti-progestogens, adrenergic agonists, analgesics, sedatives, amides, arylpiperazines, nerve agents, antineoplastics, anti-inflammatory agents, anticholinergics, anticonvulsants, antidepressants, antiepileptics, antihistaminics, antihypertensives, muscle relaxants, diuretics, bronchodilators, and glucocorticoids. Alternatively, depending on the course of treatment for the mammalian subject, any other suitable active agent may be used. The following list of active agents is purely an illustration and should not be construed as a limitation.

Hormones. In one embodiment of the invention the active agent includes any one of or a combination of steroid or nonsteroid hormones, their precursors, derivatives and analogs, esters and salts thereof including, but not limited to: dehydroepiandosterone (DHEA) and its derivatives, e.g., salts, optical isomers, racemic, androgens, estrogens and progestins (also referred to as progestogens). For example, the combination of hormones may be androgens plus estrogens, androgens plus progestogens, or androgens plus estrogens plus progestogens.

Examples of androgens which may be used in this invention include testosterone (17-β-hydroxyandrostenone), and testosterone esters, such as testosterone enanthate, testosterone propionate, testosterone decanoate and testosterone cypionate. The aforementioned testosterone esters are commercially available or may be readily prepared using techniques known to those skilled in the art or described in the pertinent literature. Also, pharmaceutically acceptable esters of testosterone and 4-dihydrotestosterone, typically esters formed from the hydroxyl group present at the C-17 position (such as enanthate, propionate, cypionate, phenylacetate, acetate, isobutyrate, buciclate, heptanoate, decanoate, undecanoate, caprate and isocaprate esters); and pharmaceutically acceptable derivatives of testosterone such as methyl testosterone, testolactone, oxymetholone and fluoxymesterone may be used.

Other suitable androgenic agents that may be used in the formulations of the present invention include, but are not limited to: the endogenous androgens, precursors and derivatives thereof, including androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, sodium dehydroepiandrosterone sulfate, 4-dihydrotestosterone (DHT), 5 adihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol, as well as androgen receptor agonists, and antiandrogens.

Examples of estrogens and progestogens which may be useful in this invention include estrogens such as 17 betaestradiol, estradiol, estradiol benzoate, estradiol 17 beta-cypionate, estriol, estrone, ethynil estradiol, mestranol, moxestrol, mytatrienediol, polyestradiol phosphate, quinestradiol, quinestrol; progestogens such as allylestrenol, anagestone, chlormadinone acetate, delmadinone acetate, demegestone, desogestrel, dimethisterone, dydrogesterone, ethynilestrenol, ethisterone, ethynodiol, ethynodiol diacetate, flurogestone acetate, gestodene, gestonorone caproate, haloprogesterone,17-hydroxy-16-methylene-progesterone, 17 alpha-hydroxyprogesterone,17 alpha-hydroxygesterone caproate, lynestrenol, medrogestone, medroxyprogesterone, megestrol acetate, melengestrol, norethindrone, norethindrone acetate, norethynodrel, norgesterone, norgestimate, norgestrel, norgestrienone, 19-norprogesterone, norvinisterone, pentagestrone, progesterone, natural progesterone, promegestone, quingestrone, trengestone.

Other Active Agents. Other suitable active agents include but are not limited to anti estrogens, such as tamoxifen, 4-OH tamoxifen; anti progestogens and anti androgens, alpha-adrenergic agonists, such as budralazine, clonidine, epinephrine, fenoxazoline, naphazoline, phenylephrine, phenylpropanolamine, beta-adrenergic agonists such as formoterol, methoxyphenamine, alpha-adrenergic blockers such as doxazosin, prazosin, terazosin, trimazosin, yohimbine, beta-adrenergic blockers such as atenolol, bisoprolol, carteolol, carvedilol, metoprolol, nadolol, penbutolol, analgesics (Narcotics or Non-Narcotics) such as buprenorphine, dihydromorphine, metazocine, methadone, morphine, morphine derivatives, nicomorphine, oxymorphone.

Sedatives. Amides. Arylpiperazines. Other suitable active agents include sedatives and anxyolitics for instance benzodiazepine derivatives such as alprazolam, bromazepam, flutazolam, ketazolam, lorazepam, prazepam; amides such as butoctamide, diethylbromoacetamide, ibrotamide, isovaleryl diethylamide, niaprazine, tricetamide, trimetozine, zolpidem, zopiclone; arylpiperazines such as buspirone Nerve Agents. Antineoplastics. Anti-inflammatory agents. Other suitable active agents include nerve agents for smoking cessation, such as nicotine, nicotine citrate and nicotine tartrate; antineoplastic agents such as 5-fluorouracil; anti-inflammatory agents; anesthetics; antianginals; anticholinergics; anticonvulsants; antidepressants; antiepileptics; anti-estrogen; antihistaminics; antiparkinsonians; bronchodilators; diuretics; glucocorticoids; muscle relaxants; narcotic antagonists; antihypothyroids such as levothyroxine, thyroid, thyroxine; antihypertensives for instance benzothiadiazine derivatives such as captopril, cilazapril, enalapril, lisinopril, perindopril, ramipril; guanidine derivatives such as guanethidine; quinazoline derivatives such as alfuzosin; reserpine derivatives such as reserpine, sulfonamide derivatives such as furosemide; others such as minoxidil, amlodipine, doxazosin mesylate, felodipine, moxonidine, nicardipine hydrochloride, nifedipine, prazosin hydrochloride, etc and calcium channel blockers such as arylalkylamines such as bepridil, ditiazem, fendiline, gallopamil, terodiline, verapamil; dihydropyridine derivatives such as felodipine, isradipine, nicardipine, nifedipine, nilvadipine, nimodipine, nisoldipine, nitrendipine, piperazine; derivatives such as flunarisine; others such as perhexiline; calcium regulator such as calcifediol, calcitonin, calcitriol, clodronic acid, dihydrotachysterol, elcatonin, etidronic acid, ipriflavone, pamidronic acid, parathyroid hormone, teriparatide acetate.

The formulation may further include a thickening agent or gelling agent present in an amount sufficient to alter the viscosity of the formulation. A gelling agent can be selected from the group including: carbomer, carboxyethylene or polyacrylic acid such as Carbopol 980 or 940 NF, 981 or 941 NF, 1382 or 1342 NF, 5984 or 934 NF, ETD 2020, 2050, 934P NF, 971P NF, 974P NF, Noveon AA-1 USP; cellulose derivatives such as ethylcellulose, hydroxypropylmethylcellulose (HPMC), ethylhydroxyethylcellulose (EHEC), carboxymethylcellulose (CMC), hydroxypropylcellulose (HPC) (Klucel different grades), hydroxyethylcellulose (HEC) (Natrosol grades), HPMCP 55, Methocel grades; natural gums such as arabic, xanthan, guar gums, alginates; polyvinylpyrrolidone derivatives such as Kollidon grades; polyoxyethylene polyoxypropylene copolymers such as Lutrol F grades 68, 127. Other gelling agents include chitosan, polyvinyl alcohols, pectins, veegum grades. A tertiary amine, such as triethanolamine or trolamine, can be included to thicken and neutralize the system.

A polymer or copolymer of acrylic acid, such as a carbomer acts as a gelling forming and facilitates the release of lipophilic active agent and penetration enhancer. Preferably, the gelling agent is Lutrol F grades and Carbopol grades. The gelling agent is present from about 0.2 to about 30.0% w/w of the formulation depending on the type of polymer. For example, the gelling agent is preferably present in an amount between about 0.5% to 2% for polyacrylic acids, and between about 1 to 5% for celluloses.

The amount and the type of the gelling agent in the formulation may be selected to provide the desired product consistency and/or viscosity to facilitate application to the skin.

Preservatives. The formulation may further include preservatives such as, but not limited to, benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative is present from about 0.01 to about 10.0% w/w depending on the type of compound.

Antioxidant. The formulation may optionally include antioxidants such as but not limited to tocopherol and derivatives, ascorbic acid and derivatives, butylated hydroxyanisole, butylated hydroxytoluene, fumaric acid, malic acid, propyl gallate, metabisulfates and derivatives. The antioxidant is present from about 0.001 to about 5.0% w/w of the formulation depending on the type of compound Buffers. The formulation may further include buffers such as carbonate buffers, citrate buffers, phosphate buffers, acetate buffers, hydrochloric acid, lactic acid, tartric acid, diethylamine, triethylamine, diisopropylamine, aminomethylamine. Although other buffers as known in the art may be included. The buffer may replace up to 100% of the water amount within the formulation.

Humectant. The formulation may further include humectant, such as but not limited to glycerin, propylene, glycol, sorbitol, triacetin. The humectant is present from about 1 to 10.0% w/w of the formulation depending on the type of compound.

Sequestering agent. The formulation may further include a sequestering agent such as edetic acid. The sequestering agent is present from about 0.001 to about 5.0% w/w of the formulation depending on the type of compound.

Surfactant. The formulation may further include anionic, non-ionic or cationic surfactants. The surfactant is present from about 0.1% to about 30.0% w/w of the formulation depending on the type of compound.

pH regulator. Optionally, the formulation may include a pH regulator, generally, a neutralizing agent, which can optionally have crosslinking function. By way of example and not limitation, the pH regulator may include a ternary amine such as triethanolamine, tromethamine, tetrahydroxypropylethylendiamine, NaOH solution. The pH regulator is present in the formulations in about 0.05 to about 2.0% w/w.

Moisturizers and Emollients. Optionally, the formulation may include moisturizers and/or emollients to soften and smooth the skin or to hold and retain moisture. By way of example and not limitation, moisturizers and emollients may include cholesterol, lecithin, light mineral oil, petrolatum, and urea.

For any particular formulation, the active agent and other ingredients may be selected to achieve the desired drug delivery profile and the amount of penetration desired. The optimum pH may also be determined and may depend on, for example, the nature of the hormone, the base, and degree of flux required.

In certain preferred embodiments of the present invention, the formulation may have the following formula.

TABLE 1

| | |
|---|---|
| Estradiol | 0.01%–2% |
| Carbomer | 0.05%–4% |
| Triethanolamine (adjust to pH 5.9) | 0.05%–1% |
| Alcohol | 20%–65% |
| Propylene glycol | 1%–15% |
| Diethylene glycol monoethyl ether | 1%–15% |
| Ion Exchange Purified Water q. ad. | 20%–65% |

TABLE 2

| | |
|---|---|
| Testosterone | 0.01%–10% |
| Carbomer | 0.05%–4% |
| Triethanolamine (adjust to pH 5.9) | 0.05%–1% |
| Alcohol | 20%–65% |
| Propylene glycol | 1%–15% |
| Diethylene glycol monoethyl ether | 1%–15% |
| Ion Exchange Purified Water q. ad. | 20%–65% |

TABLE 3

| | |
|---|---|
| Estradiol | 0.01%–1% |
| Carbomer 940 | 1.2% |
| Triethanolamine (adjust to pH 5.9) | 0.4% |
| Alcohol | 46.28% |
| Propylene glycol | 6% |
| Diethylene glycol monoethyl ether | 5% |
| Disodium EDTA | 0.06% |
| Ion Exchange Purified Water q. ad. | 100% |

TABLE 4

| | |
|---|---|
| Testosterone | 0.01%–10% |
| Carbomer 980 | 1.2% |
| Triethanolamine (adjust to pH 5.9) | 0.4% |
| Alcohol | 46.28% |
| Propylene glycol | 6% |
| Diethylene glycol monoethyl ether | 5% |
| Disodium EDTA | 0.06% |
| Ion Exchange Purified Water q. ad. | 100% |

TABLE 5

| | |
|---|---|
| Testosterone | 1% |
| Carbomer 980 | 1.2% |
| Triethanolamine (adjust to pH 5.9) | 0.4% |
| Ethanol | 47.5% |
| Propylene glycol | 6% |
| Diethylene glycol monoethyl ether | 5% |

TABLE 5-continued

| | |
|---|---|
| Disodium EDTA | 0.06% |
| Ion Exchange Purified Water q. ad. | 100% |

The formulation of the present invention is advantageous at least for the following reasons. First, the formulations of the present invention are substantially free of long-chain fatty alcohols, long-chain fatty acids, and long-chain fatty esters. Surprisingly, the formulations exhibit skin penetration sufficient to deliver an effective dosage of the desired active agent(s) to the user. This is an unexpected advantage that those of ordinary skill in the art would not have readily discovered since it had been generally understood that long-chain fatty alcohols, long-chain fatty acids, and long chain fatty esters would be required to enhance skin penetration to permit an effective dose of an active agent to penetrate the skin.

Second, because the formulation does not include aliphatic acid groups, such as fatty acids, that are commonly included in topical gels, it does not have the odor or oily texture which is associated with that ingredient as in presently-available gels. Third, the absence of long-chain fatty alcohols, long-chain fatty acids, and long-chain fatty esters means that the irritation potential is lower and that there is less chance for the components to interact, reducing the need for antioxidants or preservatives in the formulation. Numerous studies acknowledge the irritation causing potential of unsaturated fatty acids such as oleic acid. See, Tanojo H. Boelsma E, Junginger H E, Ponec M, Bodde H E, "In vivo human skin barrier modulation by topical application of fatty acids," *Skin Pharmacol Appl. Skin Physiol.* 1998 March–April; 11 (2) 87–97. It is to be understood, however, that if such preservatives are desired, the invention encompasses formulations which include antioxidants or preservatives. The reduction in the number of ingredients is advantageous at least in reducing manufacturing costs, possible skin irritation. Additionally, the reduced number of ingredients increases the storage stability of the formulation by decreasing the chance that the ingredients will interact prior to being delivered. This does not, however, imply that additional ingredients cannot be included in the formulation for particular aesthetic and/or functional effects. For example, the formulation may optionally include one or more moisturizers for hydrating the skin or emollients for softening and smoothing the skin. Glycerin is an example of such a suitable moisturizing additive.

The formulation may be applied once daily, or multiple times per day depending upon the condition of the patient. The formulation of the invention may be applied topically to any body part, such as the thigh, abdomen, shoulder, and upper arm. In one embodiment, a formulation in the form of a gel is applied to about a 5 inch by 5 inch area of skin. Application may be to alternate areas of the body as applications alternate. For example, the gel may be applied to the thigh for the first application, the upper arm for the second application, and back to the thigh for the third application. This may be advantageous in alleviating any sensitivity of the skin to repeated exposure to components of the formulation.

The invention includes the use of the formulations described above to treat subjects to increase circulating levels of active agents within the patient.

Preferred dosage units are capable of delivering an effective amount of the selected active agent over a period of about 24 hours. By an "effective" or "therapeutically effective" amount of an active agent is meant a nontoxic, but sufficient amount of the agent to provide the desired effect.

However, it will be appreciated by those skilled in the art that the desired dose will depend on the specific active agent as well as on other factors; the minimum effective dose of each active agent is of course preferred to minimize the side effects associated treatment with the selected active agent(s). The formulation is preferably applied on a regularly timed basis so that administration of the active agents is substantially continuous.

EXAMPLES

The following examples are illustrative and should not be interpreted as limiting.

Example 1

One embodiment of the formulation according to the invention is a topical gel having Testosterone 1.25% w/w, propylene glycol 5.95% w/w, Ethyl alcohol 45.46% w/w, Distilled water 45.67% w/w, Carbomer (Carbopol 980 NF) 1.21% w/w, Triethanolamine 0.39% w/w, Disodium EDTA 0.06% w/w.

Example 2

One embodiment of the formulation according to the invention is a gel composed by testosterone 1.00% w/w, diethylene glycol monoethyl ether 5.00% w/w, propylene glycol 6.00% w/w, ethanol 47.52% w/w, purified water 38.87% w/w, carbomer (CARBOPOL™ 980 NF) 1.20% w/w, triethanolamine 0.35% w/w, disodium EDTA 0.06% w/w.

Example 3

One embodiment of a formulation according to the invention is a topical hydroalcoholic gel formulation with 1% testosterone as the active ingredient. The formulation has been studied in one Phase I/II multiple dose, dose escalating clinical study in women. The study was conducted to determine the effectiveness of the formulation for the treatment of hypoactive sexual desire disorder ("HSDD"), in subjects including surgically menopausal women with low testosterone levels.

This study showed that the testosterone gel dosing between about 0.22 g to about 0.88 g formulation (2.2 to 8.8 mg/day testosterone) daily for 7 days resulted in average total and free testosterone serum concentrations within the normal range or somewhat above the normal range for pre-menopausal women.

Example 4

In vitro studies were conducted to determine the permeability profile of testosterone in human surgically excised skin using the testosterone formulation of Table 5 above (containing no lauryl alcohol, "1% T+0% LA"), as compared with other testosterone formulations containing 1% and 2% lauryl alcohol ("1% T+1% or 2% LA"). The results of these studies are presented below in Tables 6, 7 and 8.

In the first study pieces of excised human skin were mounted in Franz Vertical Diffusion Cells (Hansen Research Inc.). Approximately 10 mg of testosterone/cm² (1% T +0, 1 or 2% LA), were loaded in the loading chamber over the skin, which was maintained at 35° C. Sampling of the receptor solution was performed at selected intervals after loading. The testosterone flux and cumulative amount in the permeability study are shown below in Table 6.

TABLE 6

| Time (h) | Flux (µg/h · cm²) | | | Cum. Amt. (µg/cm²) | | | (SD) |
|---|---|---|---|---|---|---|---|
| | 0% LA | 1% LA | 2% LA | 0% LA | 1% LA | 2% LA | |
| 3 | 0.043 | 0.159 | 0.101 | 0.129 | 0.478 | 0.303 | |
| 6 | 0.093 | 0.468 | 0.307 | 0.410 | 1.884 | 1.225 | |
| 9 | 0.062 | 0.329 | 0.172 | 0.595 | 2.871 | 1.740 | |
| 12 | 0.051 | 0.165 | 0.121 | 0.748 | 3.368 | 2.104 | |
| 18 | 0.027 | 0.049 | 0.047 | 0.911 | 3.664 | 2.388 | |
| 24 | 0.026 | 0.036 | 0.052 | 1.070 | 3.883 | 2.699 | |

The testosterone flux and cumulative amount for the gel comprising approximately 1.25% testosterone, 5.00% Transcutol, 5.95% propylene glycol, 43.09% ethyl alcohol, 43.07% distilled water, 1.20% Carbopol 980NF, 0.38% triethanolamine, 0.059% EDTA are represented below in Tables 7 and 8.

TABLE 7

Testosterone In vitro flux (µg/h * cm²)*
Mean +/− S.D.

| Example 1 described above | 1.12 +/− 0.36 |
|---|---|

*(Slope of cumulative amount of permeated drug vs. time between 12 and 24 h)

TABLE 8

Testosterone
Cumulative Amount (µg/cm²)
Mean +/− S.D.

| Time (h) | Example 1 described above |
|---|---|
| 0 | 0 |
| 6 | 10.25 +/− 4.97 |
| 12 | 20.40 +/− 6.75 |
| 18 | 27.84 +/− 8.70 |
| 24 | 33.80 +/− 10.45 |

FIG. 1 is a graph depicting drug flux over time for testosterone in formulations including various amounts of lauryl alcohol (LA) in an in vitro model using human excised skin and 10 mg tosterone/cm² in the loading chamber (n=3–4±SD). The profile of 1% T+0% LA is different than the formulations containing lauryl alcohol. The profile is about 4 times lower at 6 hours than the 2% LA formulation, but overall more consistent. All profiles showed a decrease in testosterone flux after 6 hours of permeation, possibly due to drug depletion.

Another permeation study was conducted using the method described above, except that approximately 50 mg of testosterone/cm² were loaded in the loading chamber over the skin. Sampling of the receptor solution was performed at selected intervals hours after loading. The testosterone flux and cumulative amount in the permeability study are shown below.

TABLE 9

| Time (h) | Flux μg/(h · cm²) | | | Cum. μg/cm² Amt. (SD) | | |
|---|---|---|---|---|---|---|
| | 0% LA | 1% LA | 2% LA | 0% LA | 1% LA | 2% LA |
| 3.0 | 0.448 | 0.872 | 0.900 | 1.345 | 2.617 | 2.700 |
| 6.0 | 0.521 | 1.216 | 1.336 | 2.908 | 5.732 | 6.709 |
| 9.0 | 0.504 | 0.914 | 0.801 | 4.421 | 8.473 | 9.112 |

Figure 2:
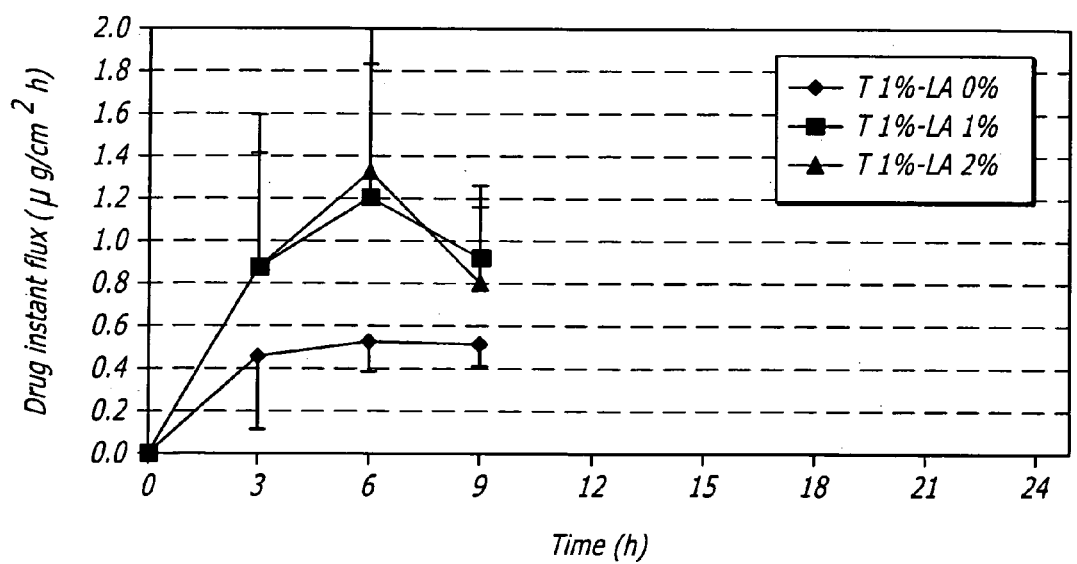
FIG. 2 is a graph depicting drug flux over time for testosterone in formulations including various amounts of lauryl alcohol (LA) in an in vitro model using human excised skin and 50 mg testosterone/cm$^2$ in the loading chamber (n=3–4±SD).

FIG. 2 is a graph depicting drug flux over time for testosterone in formulations including various amounts of lauryl alcohol (LA) in an in vitro model using human excised skin and 50 mg testosterone/cm² in the loading chamber (n=3–4±SD).

This study shows that the 1% T+0% LA has a lower permeation rate. However, the permeation profile was less variable making it potentially more desirable for use in women since testosterone levels must be titrated within a narrow range. Thus, these in vitro studies would lead one of ordinary skill in the art to believe that the inclusion of lauryl alcohol in the formulation is required in the formulation in order to achieve suitable circulating levels of hormones. However, Applicants have unexpectedly found that the inclusion of lauryl alcohol is not required in topical formulations to achieve an effective dose of circulating active agent penetration. This is especially true for Female Sexual Dysfunction where required testosterone plasmatic levels are lower than testosterone therapeutic plasmatic levels observed to treat hypogonadism.

Example 5

Experience with gel formulations and transdermal patches generally show low rates of mild dermal toxicity with the gels and extensive skin reactions with the patches, probably related to the adhesive used or the occlusive nature of the patch. For instance, with a topical gel formulation of testosterone, a few patients had skin reactions, none of which required treatment or discontinuation of drug. In contrast, transient mild to moderate erythema was observed in the majority of patients treated with a transdermal patch, and some patients had more severe reactions including blistering, necrosis, and ulceration. See for example, *Gelas B. Thébault J, Roux I, Herbrecht F. Zartarian M.*, "Comparative study of the acceptability of a new estradiol Tx 11323 (A) gel and a transdermal matrix system," Contraception, fertilité, sexualité, 1997 June; 25 (6):470–474).

Example 6

The objective of this study was to evaluate the safety and pharmacokinetic profiles of multiple doses of a 1% T+0% LA hydroalcoholic gel, in postmenopausal women. During the first 7 days of the study, the subjects received daily topical applications of 0.22 g of a formulation including 1% T+0% LA (2.2 mg/day testosterone). On Days 8–14, the subjects received 0.44 g of a formulation including 1% T+0% LA (4.4 mg/day testosterone), and on Days 15–21, the subjects received 0.88 g of a formulation including 1% T+0% LA (8.8 mg/day testosterone). There was no washout period, prior to each dose escalation. The pharmacokinetic results for total, free and bioavailable testosterone are shown below.

TABLE 10

| Parameter | Day 1 | Day 7 | Day 14 | Day 31 |
|---|---|---|---|---|
| Total Testosterone | | | | |
| Daily Dose | 2.2 mg | 2.2 mg | 4.4 mg | 8.8 mg |
| N | 7 | 7 | 7 | 7 |
| $C_o$ (ng/dL) | 21.00 (6.0) | 42.43 (14.8) | 68.71 (35.6) | 87.00 (41.6) |
| $C_{avg}$ (ng/dL) | 38.49 (17.0) | 56.03 (24.5) | 91.99 (51.2) | 141.49 (72.0) |
| $C_{max}$ (ng/dL) | 69.86 (33.0) | 113.57 (92.9) | 165.57 (113.8) | 203.86 (128.3) |
| $C_{min}$ (ng/Dl) | 19.00 (6.2) | 31.14 (15.6) | 43.14 (20.6) | 77.57 (27.9) |
| $T_{max}$ * (hr) | 20 (20–24) | 16 (1–24) | 16 (1–24) | 20 (3–24) |
| $T_{min}$ * (hr) | 1 (0–6) | 6 (0–20) | 6 (0–12) | 0 (0–12) |
| AUC (ng · hr/dL) | 923.79 (408.3) | 1344.71 (588.5) | 2207.79 (1228.1) | 3395.64 (1728.8) |
| AR (ratio) | — | 1.59 (0.7) | 2.32 (0.5) | 3.59 (0.6) |
| Free Testosterone | | | | Day 21 |
| Daily Dose | 2.2 mg | 2.2 mg | 4.4 mg | 8.8 mg |
| N | 7 | 7 | 7 | 7 |
| $C_o$ (pg/mL) | 2.64 (1.0) | 5.24 (1.8) | 7.87 (3.2) | 10.80 (7.4) |
| $C_{avg}$ (pg/mL) | 4.81 (1.8) | 6.96 (1.9) | 11.13 (5.4) | 16.69 (7.3) |
| $C_{max}$ (pg/mL) | 8.84 (3.6) | 15.79 (14.3) | 21.31 (19.5) | 25.80 (16.0) |
| $C_{min}$ (pg/mL) | 2.26 (0.9) | 3.67 (1.3) | 5.53 (2.2) | 9.23 (4.9) |
| $T_{max}$ * (hr) | 20 (20–24) | 20 (3–24) | 16 (1–24) | 20 (3–24) |
| $T_{min}$ * (hr) | 1 (0–12) | 9 (0–20) | 9 (0–12) | 0 (0–6) |
| AUC (pg hr/mL) | — | 1.57 (0.6) | 2.28 (0.5) | 3.43 (0.8) |
| Bioavailable Testosterone | | | | |
| Daily Dose | 2.2 mg | 2.2 mg | 4.4 mg | 8.8 mg |
| N | 7 | 7 | 7 | 7 |
| $C_o$ (ng/dL) | 4.01 (2.1) | 7.94 (3.7) | 12.56 (5.8) | 16.27 (12.1) |
| $C_{avg}$ (ng/dL) | 7.48 (3.4) | 10.81 (3.6) | 16.47 (8.1) | 25.04 (11.5) |

TABLE 10-continued

| Parameter | Day 1 | Day 7 | Day 14 | |
|---|---|---|---|---|
| $C_{max}$ (ng/dL) | 13.33 (6.7) | 25.57 (28.5) | 32.14 (29.4) | 39.13 (27.1) |
| $C_{min}$ (ng/dL) | 3.69 (1.7) | 5.84 (2.7) | 8.43 (3.6) | 13.84 (7.7) |
| $T_{max}$* (hr) | 20 (20–24) | 16 (1–24) | 16 (9–24) | 20 (3–24) |
| AUC (ng hr/dL) | 179.4 (81.4) | 259.52 (87.1) | 395.23 (195.0) | 600.94 (276.2) |
| AR (ratio) | — | 1.59 (0.7) | 2.26 (0.7) | 3.48 (1.2) |

Figure 3A:
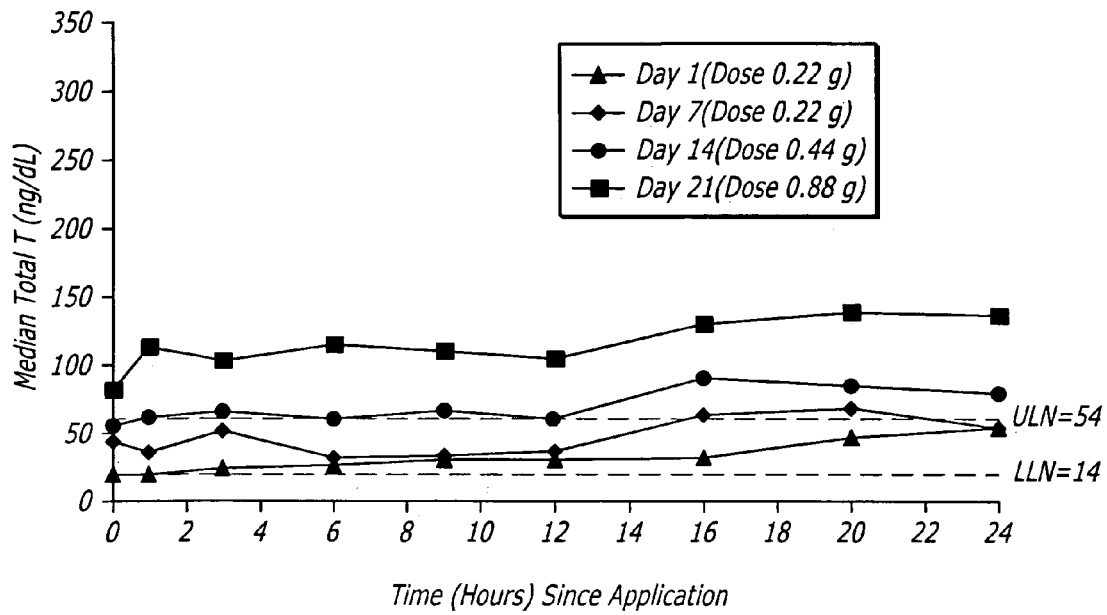
FIGS. 3A, B & C are graphs depicting median total, free and bioavailable testosterone serum concentrations following administration of 1% T+0% LA gel in vivo over a sampling period on days 1, 7, 14, and 21, respectively.
Figure 3B:
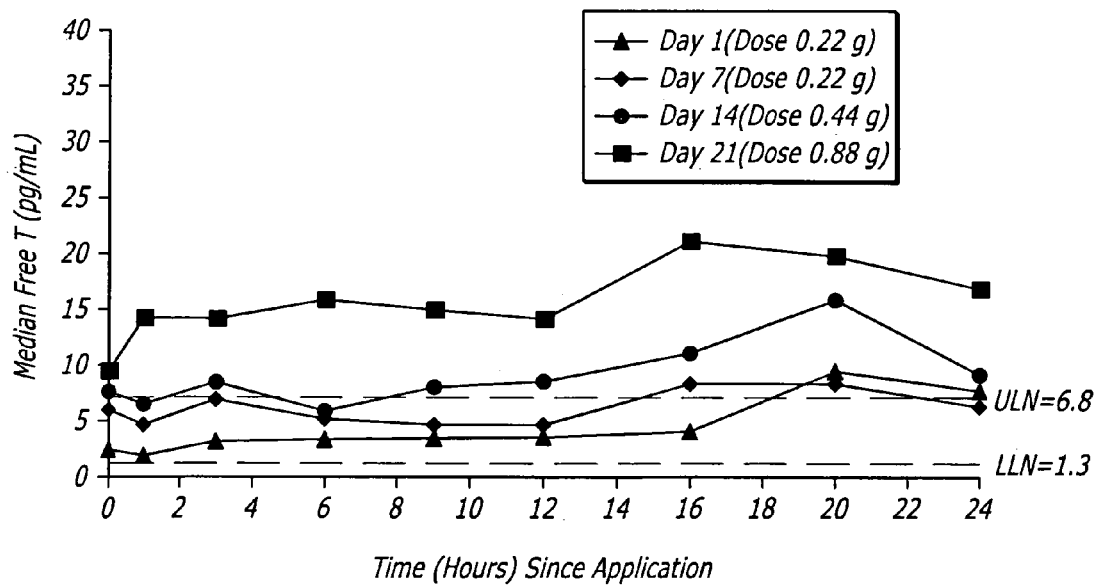
FIGS. 3D, E & F are graphs depicting mean bioavailable and free testosterone serum concentrations after different dose regimens and treatments with a 1% T+2% LA gel in vivo over a sampling period on days 1, 7, 14, respectively.
Figure 3C:
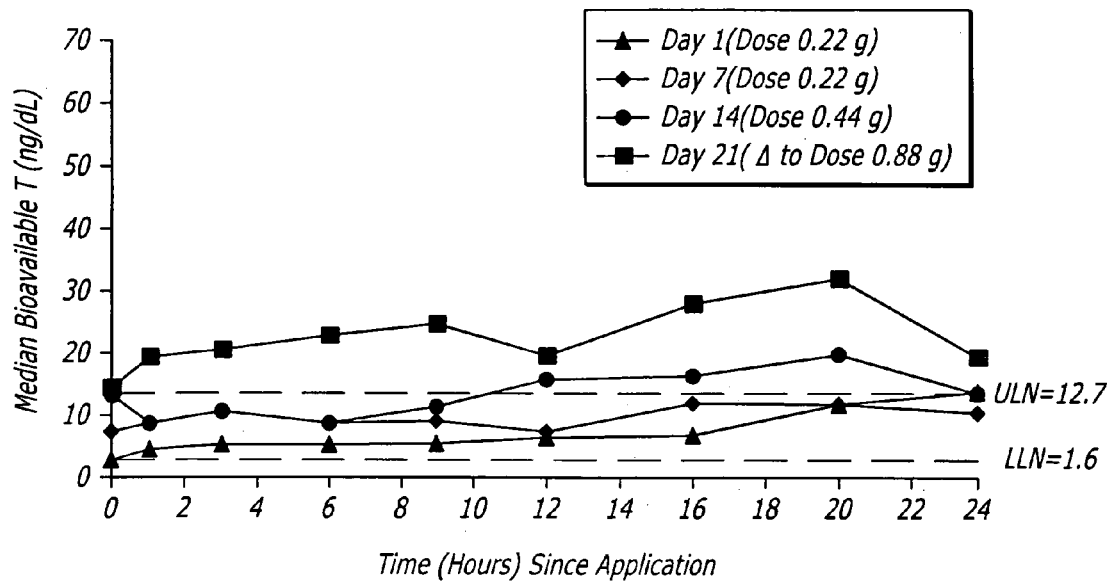

FIGS. 3A–C are graphs depicting median total, free and bioavailable testosterone serum concentrations following administration of 1% T+0% LA in vivo over a sampling period on days 1, 7, 14, and 21, respectively.

The average baseline total testosterone and free testosterone concentrations were 21.0 ng/dL and 2.6 pg/mL, respectively. After one week of 0.22 g daily doses of 1% T+0% LA, the average total testosterone and free testosterone concentrations were 56.0 ng/dL and 7.0 pg/mL, respectively. One week of daily 0.44 g doses of 1% T+0% LA increased the average total testosterone and free testosterone concentrations to 92.0 ng/dL and 11.1 pg/mL, respectively. Daily doses of 0.88 g 1% T+0% LA for 7 days increased the average testosterone and free testosterone concentrations to 141.5 ng/dL and 16.7 pg/mL in the 7 subjects.

Figure 3D:
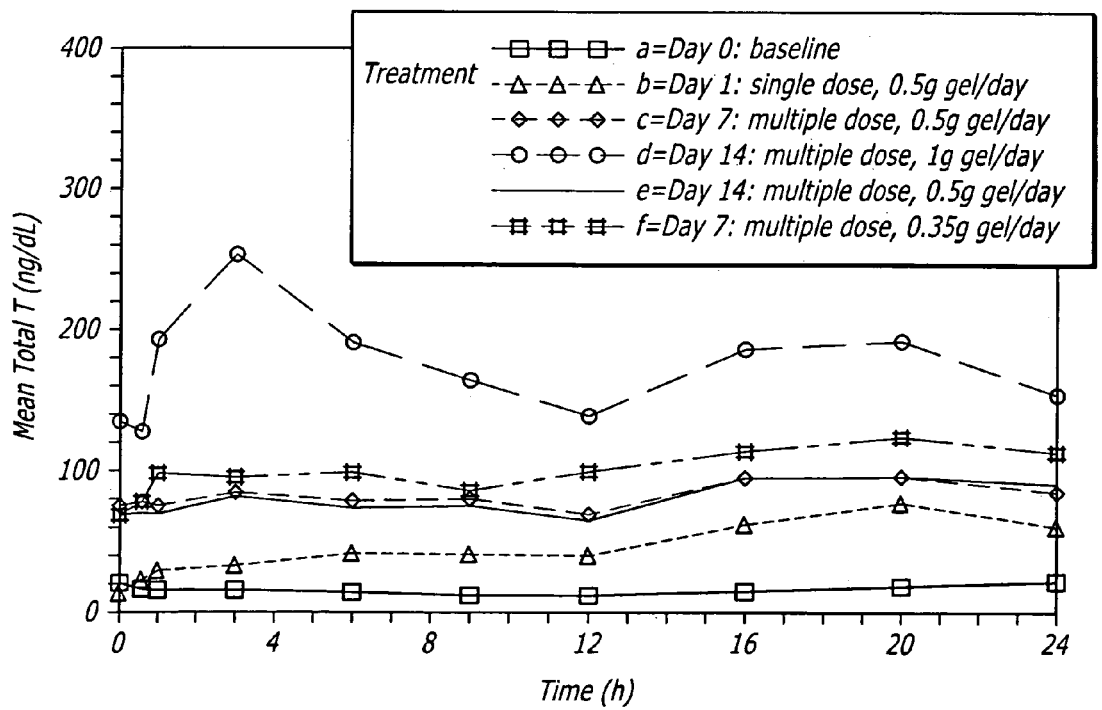
Figure 3E:
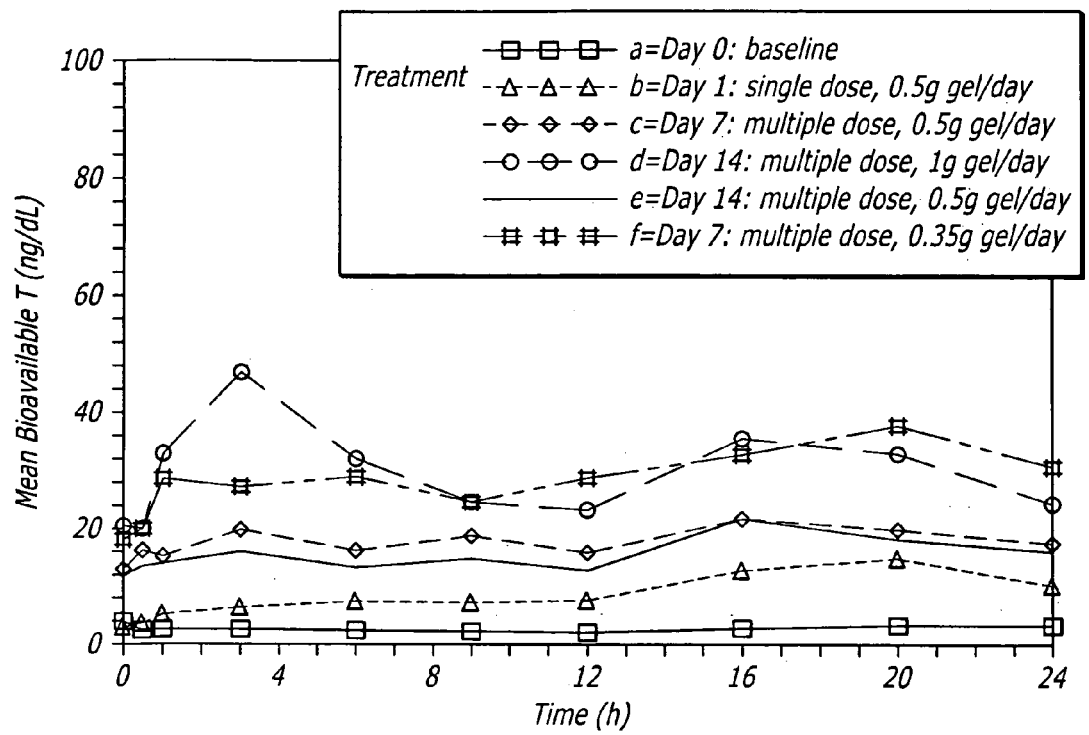
Figure 3F:
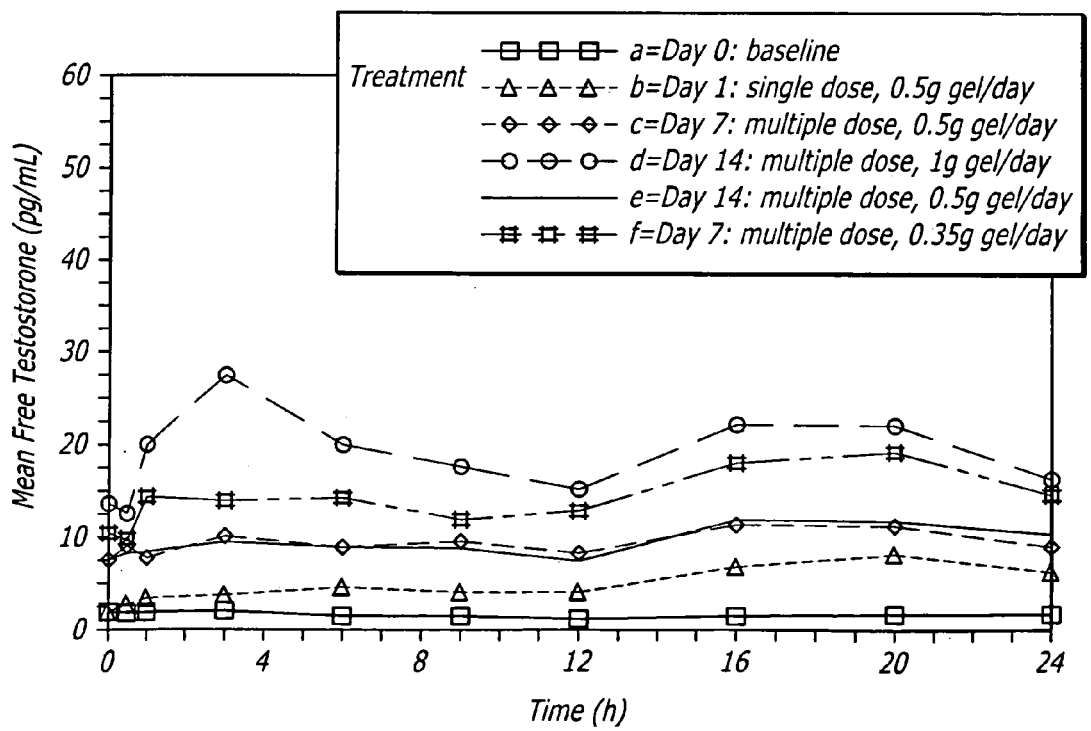

FIGS. 3D–F are graphs depicting mean bioavailable and free testosterone serum concentrations after different dose regimens and treatments with 1% T+2% LA in vivo over a sampling period on days 1, 7, 14, respectively. When like testosterone dosages are compared, this data shows that in vivo testosterone levels are not substantially changed by the inclusion of lauryl alcohol. Therefore, contrary to the in vitro findings, lauryl alcohol was not necessary to achieve effective serum levels in vivo.

This study demonstrated that 1% T 0% LA has the potential to elevate free testosterone concentrations in women with low endogenous testosterone production. The 0.22 g dose, corresponding to 2.2 mg testosterone, resulted in average free testosterone concentrations towards the upper limit of normal. For the 0.44 g dose, average free testosterone concentrations were 1.6 times the upper limit of normal while average free testosterone concentrations for the 0.88 g dose were approximately 2.4 times the upper limit of normal.

Further, the 1% T+0% LA formulation has been administered in daily testosterone doses of 2.2, 4.4, and 8.8 mg (doses of 0.22 g/day, 0.44 g/day, and 0.88 g/day, each applied for 7 days, respectively) in one Phase I/II study. The formulation was well tolerated in this study. No serious or significant adverse events were reported. No significant changes in clinical laboratory variables, vital signs, ECG parameters or physical findings were detected in any of the treatment groups.

Example 7

The primary objectives of this study were to evaluate the safety, tolerability, and pharmacokinetic profile of two different, multiple topical doses of an estradiol gel including in terms of the PK variables AUC and $C_{max}$ with and without corrections for endogenous estradiol concentrations in postmenopausal female subjects. Each subject received one of two estradiol treatments for 14 consecutive days; either 1.25 g estradiol gel 0.06% (0.75 mg estradiol/day) or 2.5 g estradiol gel 0.06% (1.5 mg estradiol/day).

Multiple doses of 0.75 mg E2/day maintained average concentrations (=AUCτ/24) of 2.4 ng/dl (24 pg/ml). The double dose of 1.5 mg E2/day resulted in an average concentration of 5.3 ng/dl (53 pg/ml). The values correspond very well to those observed after transdermal patches such as Estraderm®. When using a patch with a nominal delivery rate of 25 μg/day, an average maintenance concentration of 23 pg/ml has been reported. For patches with a delivery rates of 50 μg/day or 100 μg/day, average concentrations of 40 pg/ml and 75 pg/ml have been reported, respectively. Estraderm® has been registered in the European Community and in the United States as being efficacious for postmenopausal disorders including reduction in hot flashes, and for osteoporosis prophylaxis. Therefore, it is predicted that the E2 gel formulation will be safe and effective for treatment of menopausal symptoms including reduction of hot flashes, and for osteoporosis prophylaxis.

Figure 4A:
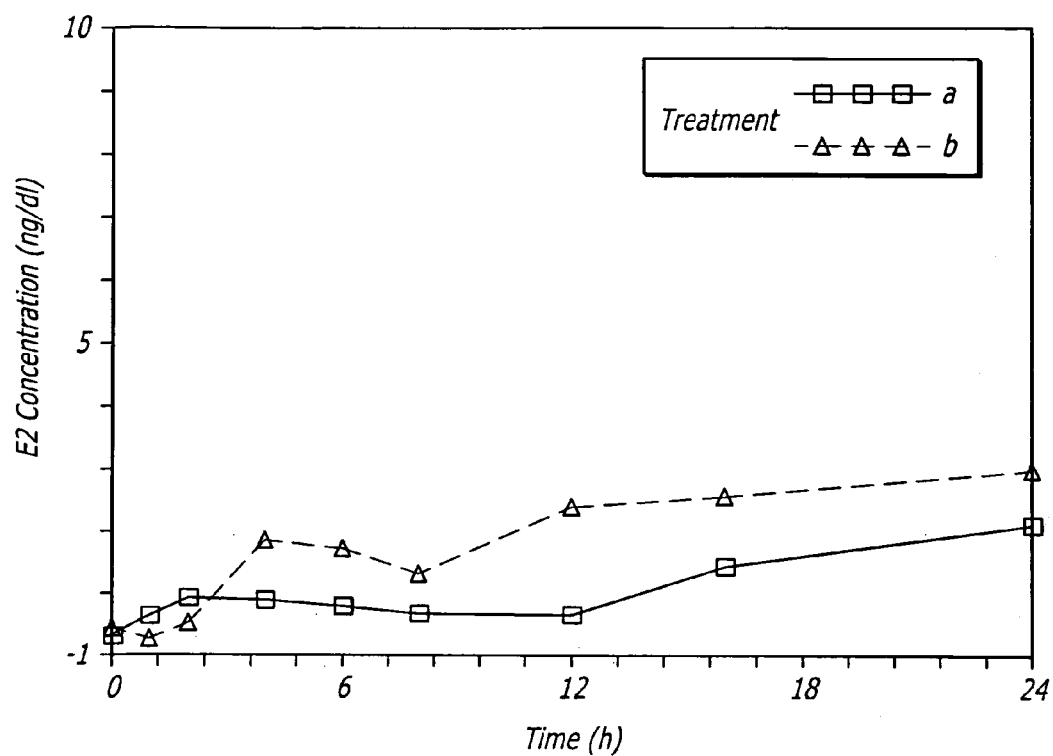
FIG. 4A is a graph depicting mean serum concentrations of estradiol (E2) following single dose administration of E2+0% LA gel (a=0.75 mg E2; b=1.50 mg E2).

Estradiol Concentration Time Data (0–24 hours) Following a Single Dose (Day 1). FIG. 4A is a graph depicting mean serum concentrations of estradiol (E2) following single dose administration of E2+0% LA gel (a=0.75 mg E2; b=1.50 mg E2). Following administration of the lower dose (treatment a), the concentration-time profile demonstrates that an increase in E2 concentrations was observed. On average, E2 concentrations increased from a baseline value of 0.4 ng/dl E2 at 0 H to 2.1 ng/dl E2 at 24 H. Following application of the higher dose, (treatment b) an increase from 0.5 ng/dl E2 at baseline at 0 H to 3.0 ng/dl E2 at 24 H was observed.

Figure 4B:
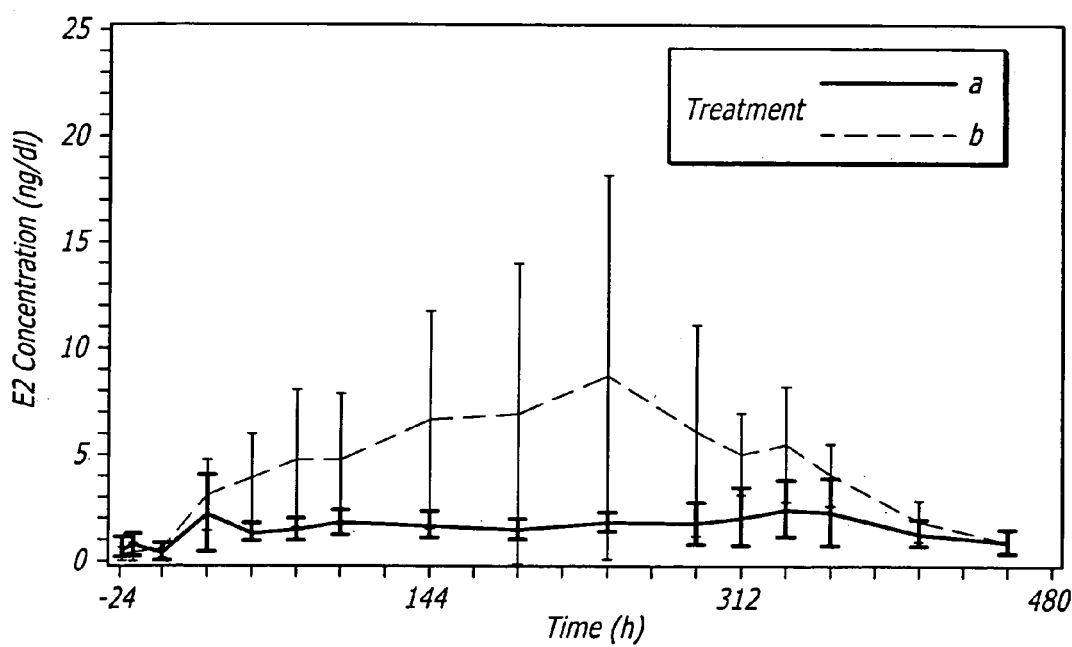
FIG. 4B is a graph depicting mean trough concentrations of E2 over time following repeated administration of E2+0% LA gel (a=0.75 mg E2; b=1.50 mg E2).
Figure 4C:
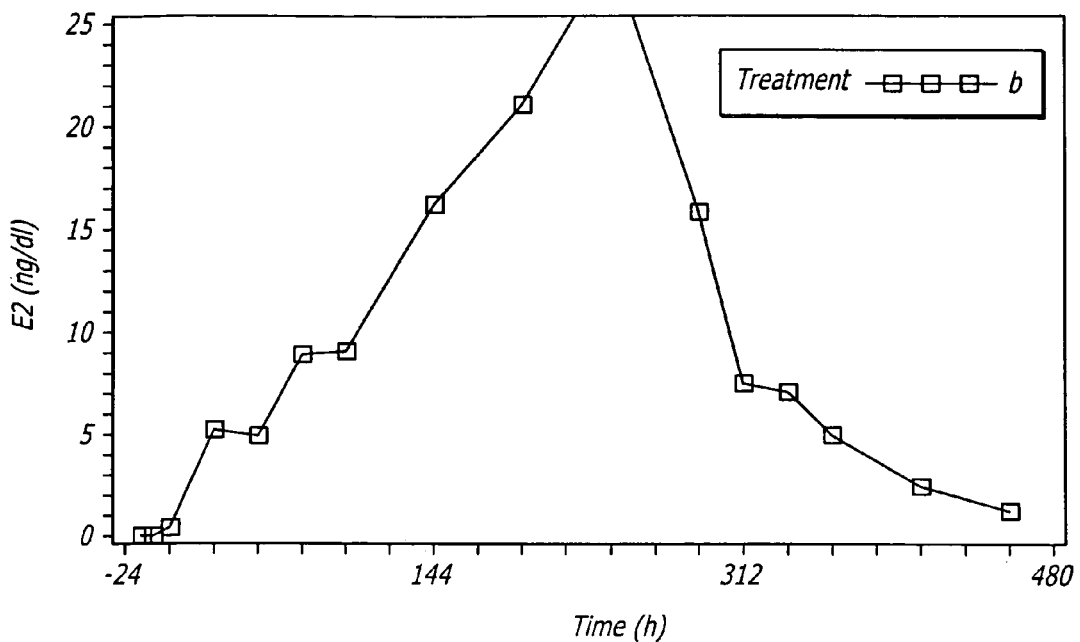
FIG. 4C is a graph depicting mean trough concentrations of E2 over time following repeated administration of E2+0% LA gel in one subject (2.5 g; ±SD; 240.0 H-value out of scale (28.0 ng/dl)).

Estradiol Trough Concentration Data (Days 1–20). FIG. 4B is a graph depicting mean trough concentrations of E2 over time following repeated administration of E2+0% LA gel. On average, the trough concentrations increased until approximately 24 H after application (Day 2, predose). Thereafter a plateau in concentrations was observed and levels fluctuated between 2.1 ng/dl at 24 H and 2.4 ng/dl E2 on the day after the last dose was applied (336 H=Day 15, 0 H). Within this sampling interval, the trough concentrations were variable and fluctuated between a minimum of 1.3 ng/dl E2 observed at 48 H (Day 3 predose) to a maximum of 2.4 ng/dl at 336 H (Day 15, 0 H). Following the last administration, average E2 concentrations declined to 0.8 ng/dl and were near predose baseline levels (0.6 ng/dl) at 456 H (Day 20, 0 H; 5 days after discontinuation of drug application).

Figure 4D:
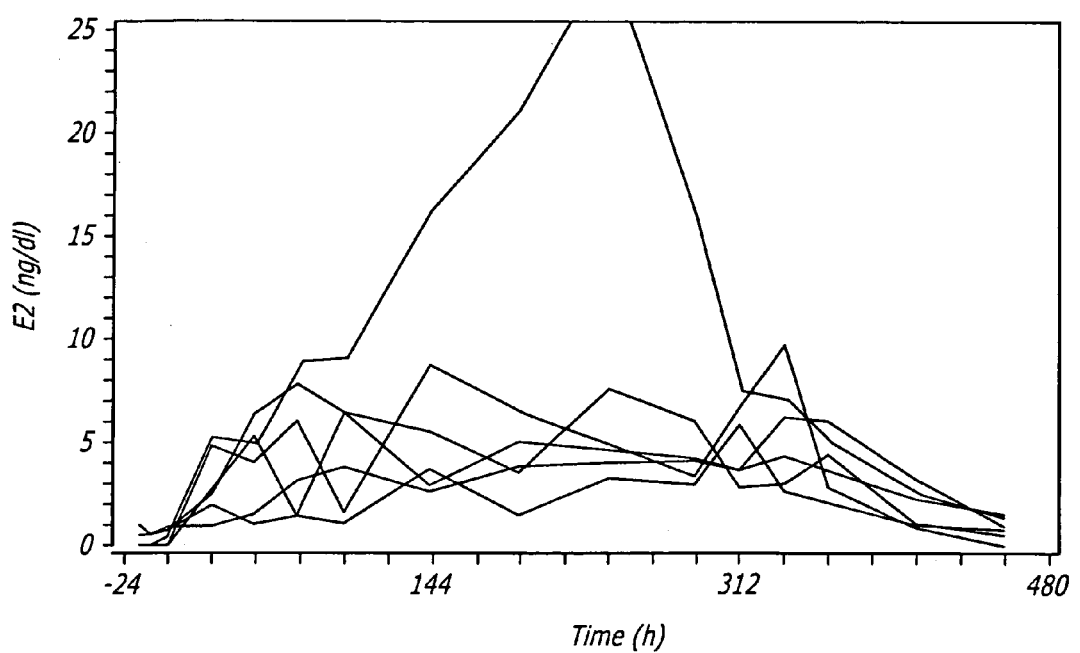
FIG. 4D is a graph depicting individual trough concentrations of E2 over time following repeated administration of E2+0% LA gel at both doses.

FIG. 4D is a graph depicting individual trough concentrations of E2 over time following repeated administration of E2+0% LA gel at both doses. On average, E2 concentrations continued to increase until approximately 240 H (Day 11 predose). Concentrations increased from 0.5 ng/dl at baseline (0 H) to 8.7 ng/dl at 240 H.

The median trough values were also examined and these reached a plateau of approximately 5.1 ng/dl E2 at 96 H (Day 5 predose) after application. Thereafter, the trough concentrations were variable and fluctuated between a minimum of 4.2 ng/dl E2 (median at 288 H, Day 13 predose) to a maximum of 5.3 ng/dl at 336 H (Day 15, 0 H). Following the last administration, average E2 concentrations declined to 0.8 ng/dl and were near predose baseline levels (0.5 ng/dl) at 456 H (Day 20, 0 H; 5 days after discontinuation of drug application). Examination of median trough concentrations indicate that steady state E2 concentrations are reached by 4 and 5 days for the E2 gel 1.25 g and 2.5 g doses, respectively.

Figure 4E:
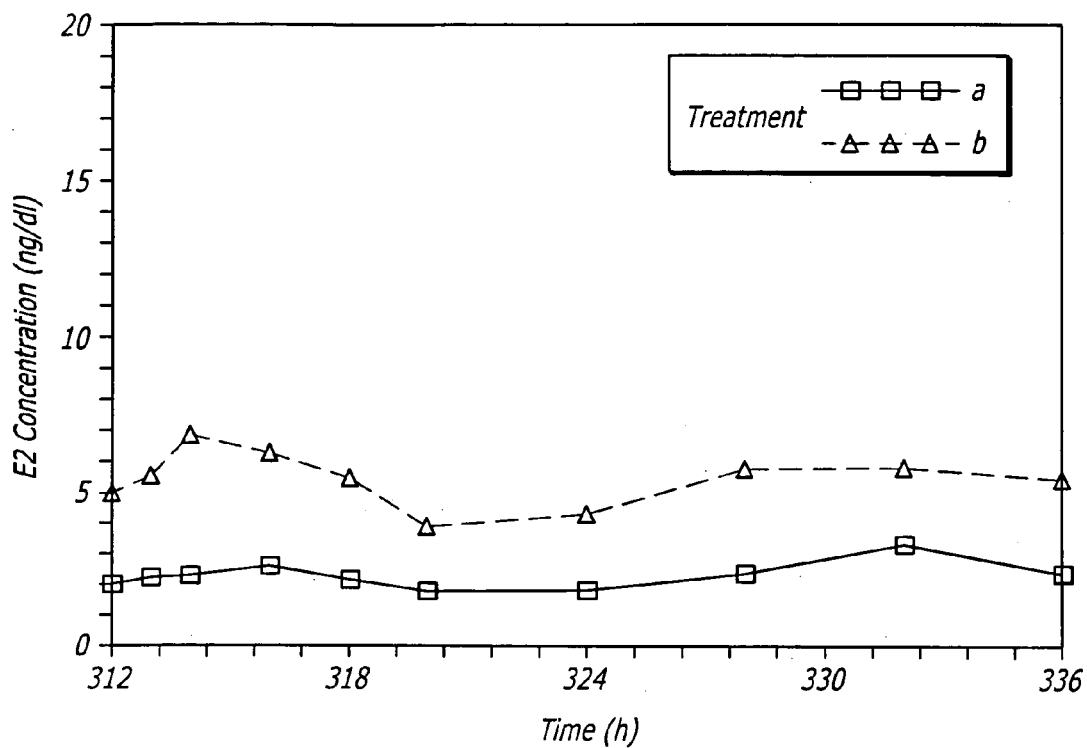
FIG. 4E is a graph depicting mean serum concentrations of E2 following multiple dose administration of E2+0% LA gel (a=0.75 mg E2; b=1.50 mg E2).

Estradiol Concentration Time Data (0–24 hours) Following 14 Doses (Day 14). FIG. 4E is a graph depicting mean serum concentrations of E2 following multiple dose administration of E2+0% LA gel. The profiles on Day 14 demonstrate that steady state E2 concentrations were reached by Day 14 (312 H). The mean E2 concentrations at the beginning of this interval (treatment a: 2.0 ng/dl E2, treatment b: 5.0 ng/dl E2) and at the end of this sampling interval (treatment a: 2.4 ng/dl E2, treatment b: 5.5 ng/dl E2) were comparable. Average maximum E2 concentrations were 3.7 ng/dl and 8.8 ng/dl, respectively (Day 14 data).

Estradiol Pharmacokinetic Parameters on Day 1 and Day 14. The pharmacokinetic parameters for E2 following single and multiple applications of Bio-E-Gel at 1.25 g and 2.5 g are presented in Table 10a. A descriptive summary of the pharmacokinetic parameters, uncorrected and baseline-adjusted, are presented in Table 10c and 10d, respectively.

Following a single application of 1.25 g of E2 gel, maximum concentrations ($C_{max}$) on Day 1 were 2.3 ng/dl. On average, the time to maximum concentrations, $t_{max}$, was achieved by 17.67 H. The exposure to E2, as measured by AUCτ was 27.5 ng/dl*H. Following multiple applications, $C_{max}$ concentrations increased to 3.7 ng/dl on Day 14. The $t_{max}$ estimates were approximately 16H on Day 14 and were comparable to those observed on Day 1. The exposure to E2 was 57.0 ng/dl*H on Day 14 and was higher than that observed on Day 1, demonstrating the accumulation of E2 in the serum following repeated applications.

Following a single application of 2.5 g of E2 gel, maximum concentrations ($C_{max}$) on Day 1 were 3.7 ng/dl. On average, the time to maximum concentrations, $t_{max}$, was achieved by 18 H. The exposure to E2, as measured by AUCτ was 49.7 ng/dl*H. Following multiple application, $C_{max}$ concentrations increased to 8.8 ng/dl on Day 14. The $t_{max}$ estimates were approximately 18 H on Day 14 and were comparable to those observed on Day 1. The exposure to E2 was 128.2 ng/dl*H on Day 14 and was higher than that observed on Day 1, demonstrating the accumulation of E2 in the serum following repeated applications.

The ratio of geometric means of E2 gel 2.5 g/1.25 g was used to assess the dose proportionality of E2 following the two doses of E2 gel. After single dose application, the mean AUC ratio (E2 gel 2.5 g/1.25 g) was 38.4/19.2=2.0 and after multiple doses it was 117.6/51.9=2.3, indicating dose proportionality.

TABLE 10a

E2 - PK Variables by Dose Regimens

| Variable | Statistic | 1.25 g Bio-E-Gel, Single Dose | 1.25 g Bio-E-Gel, Multiple Dose | 2.5 g Bio-E-Gel, Single Dose | 2.5 g Bio-E-Gel, Multiple Dose |
|---|---|---|---|---|---|
| AUCτ [ng/dl * H] | N | 6 | 6 | 6 | 6 |
| | Mean | 27.5 | 57.0 | 49.7 | 128.2 |
| | SD | 17.2 | 29.9 | 48.1 | 50.0 |
| | GeoM | 19.2 | 51.9 | 38.4 | 117.6 |
| | G_CV | 173.5 | 48.0 | 79.0 | 53.1 |
| $C_{max}$ [ng/dl] | N | 6 | 6 | 6 | 6 |
| | Mean | 2.3 | 3.7 | 3.7 | 8.8 |
| | SD | 1.8 | 2.3 | 2.7 | 4.8 |
| | GeoM | 1.7 | 3.2 | 3.1 | 7.6 |
| | G_CV | 110.1 | 54.2 | 75.9 | 67.0 |
| $t_{max}$ [H] | N | 6 | 6 | 6 | 6 |
| | Mean | 17.67 | 327.83 | 18.00 | 330.33 |
| | SD | 8.62 | 9.85 | 4.90 | 8.62 |
| | Min | 2.00 | 313.00 | 12.00 | 314.00 |
| | Med | 20.00 | 332.00 | 16.00 | 334.00 |
| | Max | 24.00 | 336.00 | 24.00 | 336.00 |
| Baseline, $C_0$ [ng/dl] | N | 6 | 6 | 6 | 6 |
| | Mean | 0.5 | 0.5 | 0.4 | 0.4 |
| | SD | 0.4 | 0.4 | 0.3 | 0.3 |
| | Min | 0.0 | 0.0 | 0.0 | 0.0 |
| | Med | 0.5 | 0.5 | 0.4 | 0.4 |
| | Max | 1.3 | 1.3 | 0.8 | 0.8 |

Baseline Adjusted Estradiol Pharmacokinetic Parameters on Day 1 and Day 14. Baseline concentrations of E2 were similar for both groups and were calculated as 0.5 ng/dl and 0.4 ng/dl for the 1.25 g and 2.5 g E2 gel, respectively. In order to correct for endogenous E2 concentrations, the baseline E2 concentration (E2 gel 1.25 g: 0.5 ng/dl and 2.5 g: 0.4 ng/dl) was subtracted from the total concentration measured after application and the AUCτ and $C_{max}$ were recalculated based on the baseline-adjusted concentration. The results of the baseline-adjusted pharmacokinetic variables are summarized in Table 10b. The baseline-adjusted $C_{max}$ estimates were 1.8 ng/dl and 3.4 ng/dl following single applications of the 1.25 g and 2.5 g E2 gel, respectively. For AUCτ, the baseline-adjusted values were 14.9 ng/dL*H and 41.4 ng/dl*H for the 1.25 g and 2.5 g E2 gel, respectively. Following repeated applications, $C_{max}$ estimates increased to 3.1 ng/dl and 8.4 ng/dl and AUCτ estimates increased to 44.2 ng/dl*H and 119.6 ng/dl*H for 1.25 g and 2.5 g E2 gel, respectively. These increases reflect the accumulation of drug in the serum following repeated application of the gel.

The terminal elimination half-life (t½) of E2 was calculated from the baseline-adjusted concentrations following the last dose (at 312 H, Day 14 predose) by log-linear regression from the linear portion of the logarithmic transformed concentration-time plot. The individual and mean estimates of half-life following the application of 1.25 g and 2.5 g E2 gel are presented in Table 10d. The median half-life was 22.15 H (range: 13.11–76.71) for E2 gel 1.25 g and 35.58 H (range: 26.60–51.59) for 2.5 g. The half-life estimates for both treatment groups were comparable.

TABLE 10b

E2 - PK Variables, Baseline Adjusted

| Variable | Statistic | 1.25 g, Single Dose | 1.25 g, Multiple Dose | 2.5 g, Single Dose | 2.5 g, Multiple Dose |
|---|---|---|---|---|---|
| δAUCτ [ng/dl * H] | N | | | | |
| | Mean | 14.9 | 44.2 | 41.4 | 119.6 |
| | SD | 13.3 | 22.2 | 51.1 | 51.2 |

TABLE 10b-continued

E2 - PK Variables, Baseline Adjusted

| Variable | Statistic | 1.25 g, Single Dose | 1.25 g, Multiple Dose | 2.5 g, Single Dose | 2.5 g, Multiple Dose |
|---|---|---|---|---|---|
| | GeoM | 9.8 | 39.7 | 25.2 | 108.9 |
| | G_CV | 147.3 | 56.1 | 139.6 | 53.5 |
| $\delta C_{max}$ [ng/dl] | N | 6 | 6 | 6 | 6 |
| | Mean | 1.8 | 3.1 | 3.4 | 8.4 |
| | SD | 1.8 | 2.0 | 2.9 | 4.7 |
| | GeoM | 1.2 | 2.7 | 2.4 | 7.3 |
| | G_CV | 132.8 | 56.4 | 118.5 | 68.5 |
| $t_{1/2}$ [H] | N | | 4 | | 4 |
| | Mean | | 33.53 | | 37.34 |
| | SD | | 29.16 | | 12.41 |
| | Min | | 13.11 | | 26.60 |
| | Med | | 22.15 | | 35.58 |
| | Max | | 76.71 | | 51.59 |

Figure 4F:
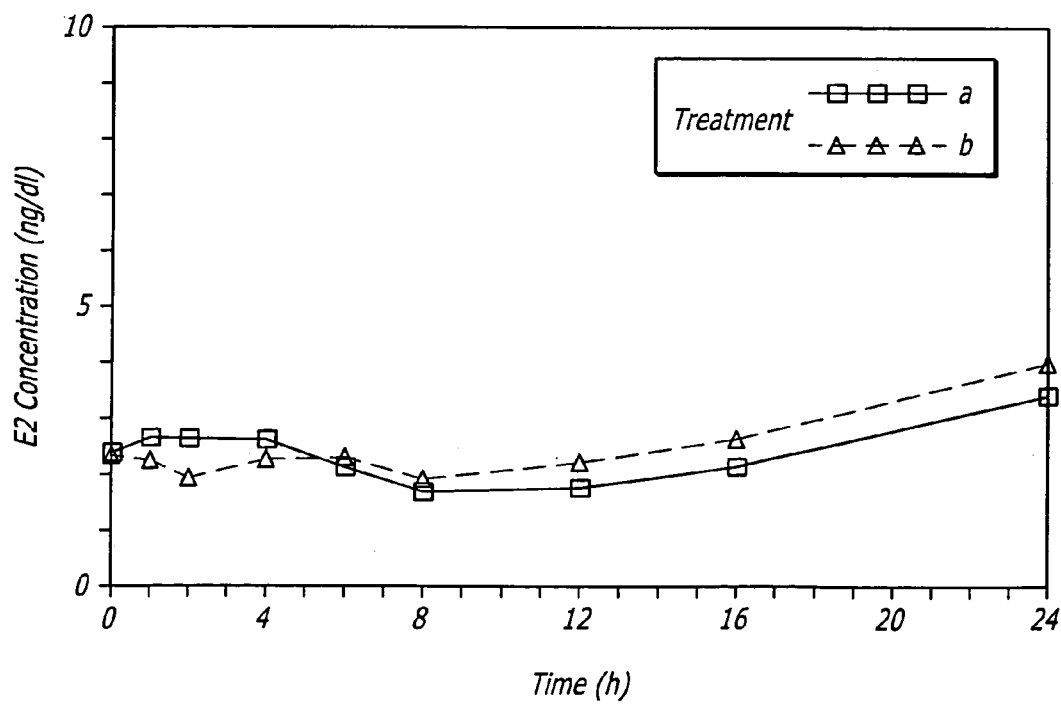
FIG. 4F is a graph depicting mean serum concentrations of estrone (E1) following single dose administration of E2+0% LA gel (a=0.75 mg E2; b=1.50 mg E2).

Estrone Concentration Time Data (0–24 hours) Following a Single Dose (Day 1). FIG. 4F is a graph depicting mean serum concentrations of estrone (E1) following single dose administration of E2+0% LA gel. On average, E1 concentrations increased from a baseline value of 2.4 ng/dl E1 at 0 H to 3.4 ng/dl E1 at 24 H. Following application of the higher dose, (treatment b) an increase from 2.4 ng/dl E1 at baseline (0 H) to 4.0 ng/dl E1 at 24 H was observed.

Figure 4G:
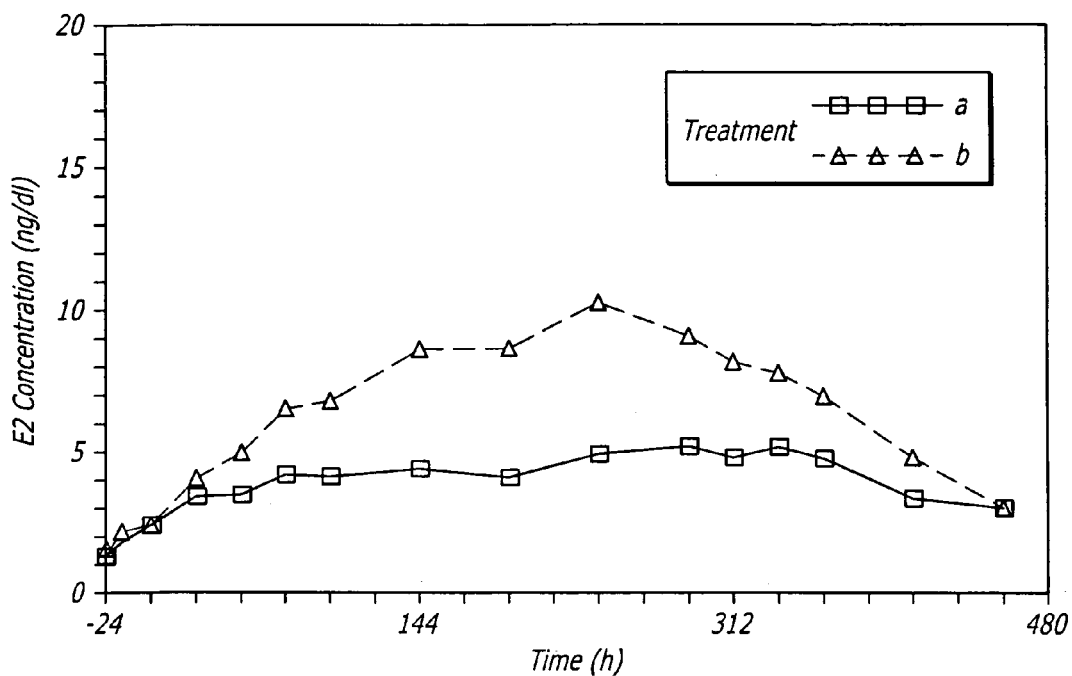
FIG. 4G is a graph depicting mean trough concentrations of E1 following repeated administration of E2+0% LA gel (a=0.75 mg E2; b=1.50 mg E2).

Estrone Trough Concentration Data (Days 1–20). FIG. 4G is a graph depicting mean trough concentrations of E1 following repeated administration of E2+0% LA gel. On average, the trough concentrations increased to approximately 72 H (Day 4 predose) after application. Thereafter a plateau in concentrations was observed and levels fluctuated between 4.3 ng/dl at 72 H and 5.2 ng/dl E1 on the day after the last dose was applied (336 H=Day 15, 0 H). Within this sampling interval, the trough concentrations were variable and fluctuated between a minimum of 4.1 ng/dl E1 observed at 96 H (Day 5 predose) to a maximum of 5.3 ng/dl at 288 H (Day 13 predose). Following the last administration, average E1 concentrations declined to 3.0 ng/dl and were near predose baseline levels (2.4 ng/dl) at 456 H (Day 20, 0 H; 5 days after discontinuation of drug application).

The mean E1 trough concentrations following repeated administration of Bio-E-Gel 2.5 g are also presented in FIG. 4G. On average, E1 concentrations continued to increase until approximately 240 H (Day 11 predose). Concentrations increased from 2.4 ng/dl at baseline (0 H) to 10.4 ng/dl at 240 H. Thereafter, the trough concentrations were variable and fluctuated between 9.1 ng/dl E1 (at 288 H=Day 13 predose) to 7.8 ng/dl at 336 H (Day 15, 0 H). Following the last administration, average E1 concentrations declined to 3.1 ng/dl and were near predose baseline levels (4.0 ng/dl) at 456 H (Day 20, 0 H; 5 days after discontinuation of drug application). Examination of mean trough concentrations indicate that steady state E1 concentrations are reached by 11 and 13 days for the Bio-E-Gel 2.5 g and 1.25 g doses, respectively.

Figure 4H:
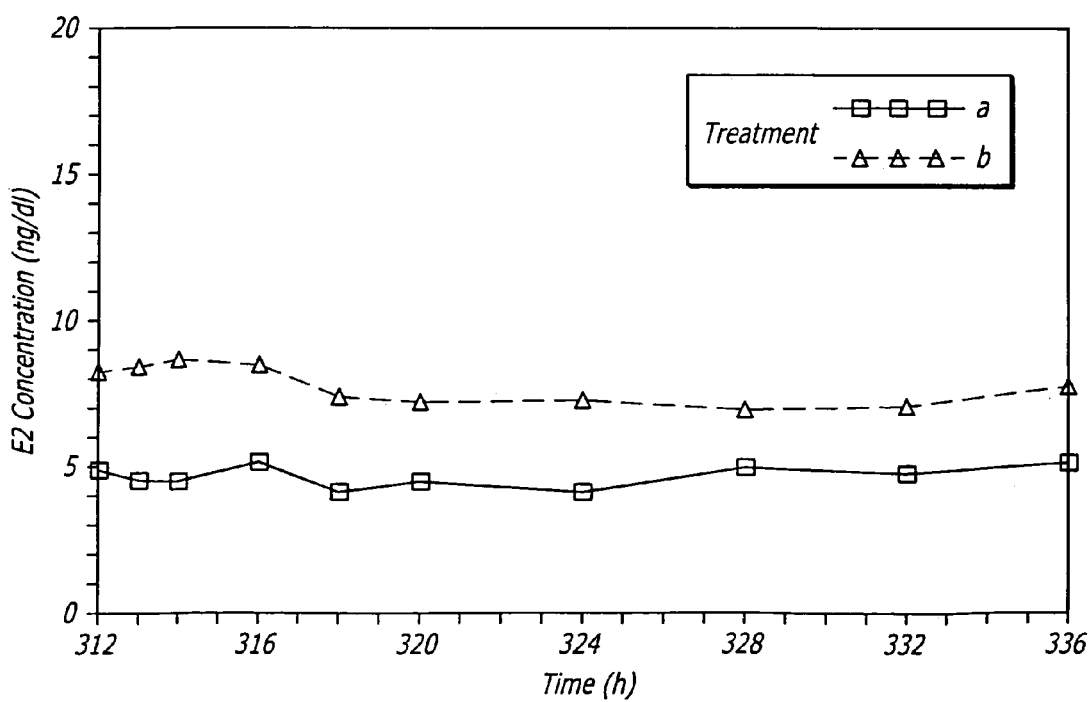
FIG. 4H is a graph depicting mean serum concentrations of E1 following multiple dose administration of E2+0% LA gel (a=0.75 mg E2; b=1.50 mg E2).

Estrone Concentration Time Data (0–24 hours) Following 14 Doses (Day 14). FIG. 4H is a graph depicting mean serum concentrations of E1 following multiple dose administration of E2+0% LA gel. The profiles on Day 14 demonstrate that steady state E1 concentrations were reached by Day 14 (312 H). The E1 concentrations at the beginning of this interval (treatment a: 4.8 ng/dl, treatment b: 8.2 ng/dl) and at the end of this sampling interval (treatment a: 5.2 ng/dl, treatment b: 7.8 ng/dl) were comparable. Average maximum E1 concentrations on Day 14 (312 to 336 H) were 6.0 ng/dl and 9.2 ng/dl, respectively.

Estrone Pharmacokinetic Parameters on Day 1 and Day 14. Following a single application of 1.25 g of E2 gel, maximum concentrations ($C_{max}$) on Day 1 were 3.6 ng/dl. On average, the time to maximum concentrations, $t_{max}$, was achieved by 12.67 H. The exposure to E1, as measured by AUCτ was 56.2 ng/dl*H. Following multiple applications, Cmax concentrations increased to 6.0 ng/dl on Day 14. The $t_{max}$ estimates were approximately 11 H on Day 14 and were comparable to those observed on Day 1. The exposure to E1 was 111.4 ng/dl*H on Day 14 and was higher than that observed on Day 1, demonstrating the accumulation of E1 in the serum following repeated applications.

Following a single application of 2.5 g of E2 gel, maximum concentrations ($C_{max}$) on Day 1 were 4.1 ng/dl. On average, the time to maximum concentrations, $t_{max}$, was achieved by 21 H. The exposure to E1, as measured by AUCτ was 62.2 ng/dl*H. Following multiple application, $C_{max}$ concentrations increased to 9.2 ng/dl on Day 14. The $t_{max}$ estimates were approximately 2 H on Day 14 and were lower than those observed on Day 1. The exposure to E1 was 179.7 ng/dl*H on Day 14 and was higher than that observed on Day 1, demonstrating the accumulation of E1 in the serum following repeated applications.

TABLE 10c

E1 - PK Variables by Dose Regimens

| Variable | Statistic | 1.25 g Single Dose | 1.25 g Multiple Dose | 2.5 g Single Dose | 2.5 g Multiple Dose |
|---|---|---|---|---|---|
| AUCτ [ng/dl * H] | N | 6 | 6 | 6 | 6 |
| | Mean | 56.2 | 111.4 | 62.2 | 179.7 |
| | SD | 31.2 | 54.2 | 30.0 | 67.6 |
| | GeoM | 49.6 | 100.8 | 56.2 | 167.1 |
| | G_CV | 59.2 | 51.9 | 53.2 | 46.3 |
| $C_{max}$ [ng/dl] | N | 6 | 6 | 6 | 6 |
| | Mean | 3.6 | 6.0 | 4.1 | 9.2 |
| | SD | 1.6 | 2.7 | 0.6 | 3.1 |
| | GeoM | 3.2 | 5.6 | 4.0 | 8.7 |
| | G_CV | 56.3 | 45.0 | 13.2 | 40.5 |
| $t_{max}$ [H] | N | 6 | 6 | 6 | 6 |
| | Mean | 12.67 | 323.33 | 21.01 | 314.33 |
| | SD | 12.42 | 9.93 | 7.33 | 1.51 |
| | Min | 1.00 | 312.00 | 6.05 | 312.00 |
| | Med | 13.00 | 322.00 | 24.00 | 314.00 |
| | Max | 24.00 | 336.00 | 24.00 | 316.00 |
| Baseline, $C_0$ [ng/dl] | N | 6 | 6 | 6 | 6 |
| | Mean | 1.8 | 1.8 | 2.0 | 2.0 |
| | SD | 1.4 | 1.4 | 0.9 | 0.9 |
| | Min | 0.5 | 0.5 | 1.1 | 1.1 |
| | Med | 1.5 | 1.5 | 1.8 | 1.8 |
| | Max | 4.4 | 4.4 | 3.2 | 3.2 |

Baseline Adjusted Estrone Pharmacokinetic Parameters on Day 1 and Day 14. Baseline concentrations of E1 were similar for both groups and were calculated as 1.8 ng/dl and 2.0 ng/dl for the 1.25 g and 2.5 g E2 gel, respectively. In order to correct for endogenous E1 concentrations, the baseline E1 concentration (E2 gel 1.25 g: 1.8 ng/dl and E2 gel 2.5 g: 2.0 ng/dl) was subtracted from the total concentration measured after application and the AUCτ and $C_{max}$ were recalculated based on the baseline-adjusted concentration. The results of the baseline-adjusted pharmacokinetic variables are summarized in Table 10d. The baseline-adjusted $C_{max}$ estimates were 1.8 ng/dl and 2.0 ng/dl following single applications of the 1.25 g and 2.5 g E2 gel respectively. For AUCτ, the baseline-adjusted values were 14.5 ng/dL*H and 17.9 ng/dl*H for the 1.25 g and 2.5 g E2 gel, respectively. Following repeated applications, $C_{max}$ estimates increased to 4.2 ng/dl and 7.2 ng/dl and AUCτ estimates increased to 67.1 ng/dl*H and 131.2 ng/dl*H for 1.25 g and 2.5 g E2 gel, respectively. These increases reflect the accumulation of drug in the serum following repeated application of the gel.

TABLE 10d

E1 - PK Variables, Baseline Adjusted

| Variable | Statistic | 1.25 g Single Dose | 1.25 g Multiple Dose | 2.5 g Single Dose | 2.5 g Multiple Dose |
|---|---|---|---|---|---|
| δAUC$_\tau$ [ng/dl * H] | N | 6 | 6 | 6 | 6 |
| | Mean | 14.5 | 67.1 | 17.9 | 131.2 |
| | SD | 5.6 | 27.1 | 6.0 | 68.4 |
| | Med | 14.6 | 63.9 | 16.2 | 139.6 |
| | GeoM | 13.6 | 63.0 | 17.2 | 113.8 |
| | G_CV | 42.1 | 39.9 | 31.3 | 68.0 |
| δC$_{max}$ [ng/dl] | N | 6 | 6 | 6 | 6 |
| | Mean | 1.8 | 4.2 | 2.0 | 7.2 |
| | SD | 0.8 | 1.7 | 0.5 | 3.2 |
| | Med | 1.7 | 3.6 | 2.0 | 8.0 |
| | GeoM | 1.6 | 4.0 | 2.0 | 6.4 |
| | G_CV | 47.2 | 34.7 | 30.6 | 57.5 |

Figure 4I:
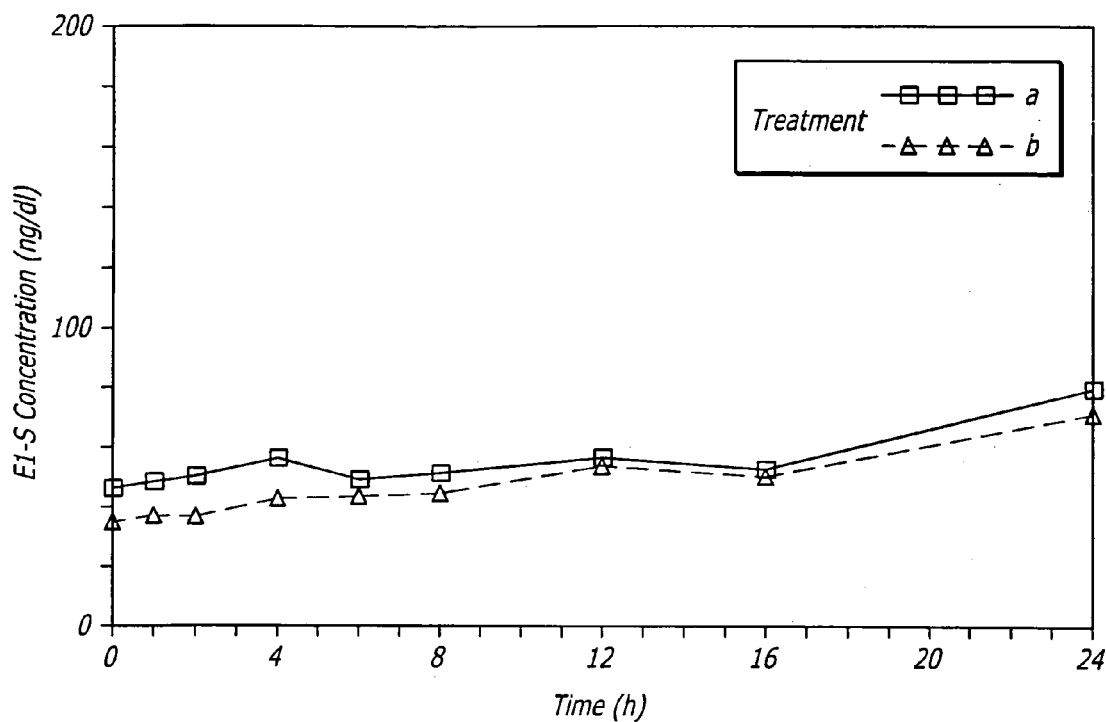
FIG. 4I is a graph depicting mean serum concentrations of estrone-sulfate (E1-sulfate) following single dose administration of E2+0% LA gel (a=0.75 mg E2; b=1.50 mg E2).

Estrone-Sulfate Concentration Time Data (0–24 hours) Following a Single Dose (Day 1). FIG. 4I is a graph depicting mean serum concentrations of estrone-sulfate (E1-sulfate) following single dose administration of E2+0% LA gel (a=0.75 mg E2; b=1.50 mg E2). On average, E1-S concentrations increased from a baseline value of 45.8 ng/dl E1 at 0 H to 79.0 ng/dl E1-S at 24 H. Following application of the higher dose, (treatment b) an increase from 34.7 ng/dl E1-S at baseline at 0 H to 70.7 ng/dl E1-S at 24 H was observed.

Figure 4J:
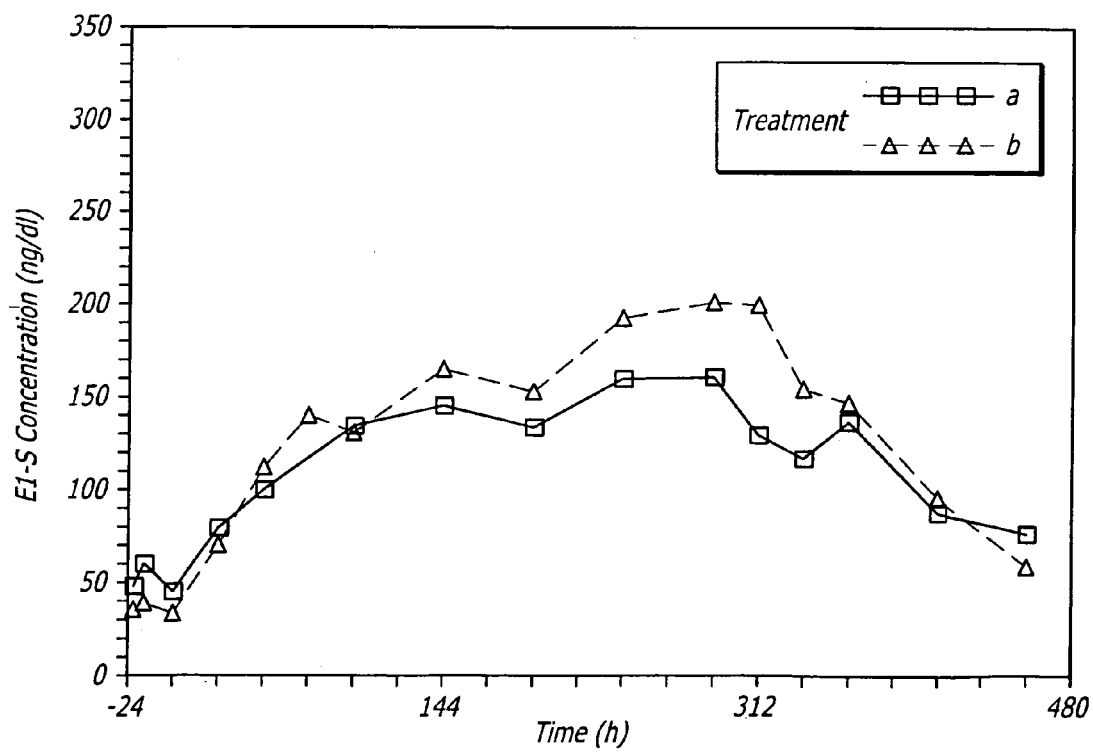
FIG. 4J is a graph depicting mean trough concentrations of E1-sulfate following multiple dose administration of E2+0% LA gel (a=0.75 mg E2; b=1.50 mg E2).

Estrone-Sulfate Trough Concentration Data (Days 1–20). FIG. 4J is a graph depicting mean trough concentrations of E1-sulfate following multiple dose administration of E2+0% LA gel (a=0.75 mg E2; b=1.50 mg E2). On average, the trough concentrations continued to increase with repeated applications although the mean plot suggested a change in the rate of increase by approximately 192 H (Day 9 predose). E1-S serum concentrations fluctuated between 133.8 ng/dl at 192 H and 117.8 ng/dl E1-S on the day after the last dose was applied (336 H; Day 15, 0 H). Following the last administration, average E1-S concentrations declined to 77.0 ng/dl and were higher than predose baseline levels (45.8 ng/dl) at 456 H (Day 20, 0 H; 5 days after discontinuation of drug application).

On average, E1-S concentrations continued to increase until approximately 312 H (Day 14 predose) although a change in the rate of increase was evident at approximately 240 H (Day 11 predose). Concentrations increased from 34.7 ng/dl at baseline (0 H) to 193.5 ng/dl at 240 H. Thereafter, the trough concentrations were variable and fluctuated between 193.5 ng/dl E1 (at 240 H) to 155.7 ng/dl at 336 H (Day 15, 0 H). Following the last administration, average E1-S concentrations declined to 60.3 ng/dl and were higher than predose baseline levels (34.7 ng/dl) at 456 H (Day 20, 0 H; 5 days after discontinuation of drug application). Examination of mean trough concentrations indicate that steady state E1-sulfate concentrations are reached by 13 and 14 days for the E2 gel 1.25 g and 2.5 g doses, respectively.

Figure 4K:
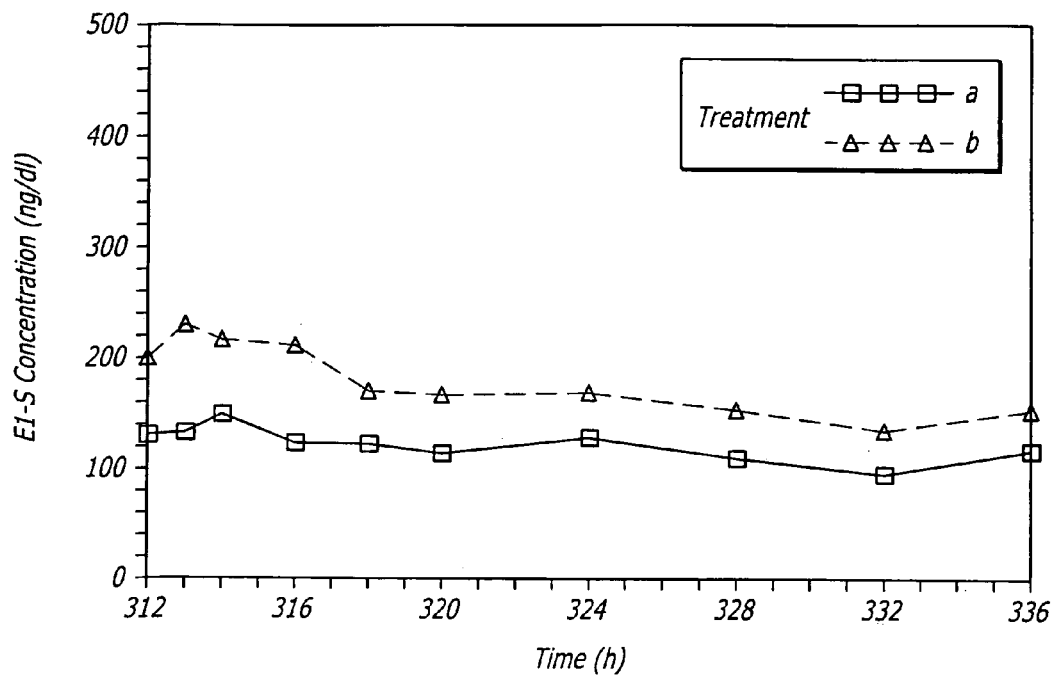
FIG. 4K is a graph depicting mean serum concentrations of E1-sulfate following multiple dose administration of E2+0% LA gel (a=0.75 mg E2; b=1.50 mg E2).

Estrone-Sulfate Concentration Time Data (0–24 hours) Following 14 Doses (Day 14). FIG. 4K is a graph depicting mean serum concentrations of E1-sulfate following multiple dose administration of E2+0% LA gel. The profiles on Day 14 demonstrate that steady state E1-S concentrations were essentially reached by Day 14 (312 H). The mean E1-S concentrations at the beginning of this interval (treatment a: 130.7 ng/dl, treatment b: 200.3 ng/dl) and at the end of this sampling interval (treatment a: 117.8 ng/dl, treatment b: 155.7 ng/dl) were slightly different. However, the range of the values overlapped thereby suggesting the comparability of the results. Average maximum E1-S concentrations on Day 14 were 163.5 ng/dl E1-S for E2 gel 1.25 g and 253.8 ng/dl E1-S for E2 gel 2.5 g.

Estrone-Sulfate Pharmacokinetic Parameters on Day 1 and Day 14. The pharmacokinetic parameters for E1-S following single and multiple applications of E2 gel at 1.25 g and 2.5 g are presented in Table 10e. A descriptive summary of the pharmacokinetic parameters, uncorrected and baseline-adjusted, are presented in Table 10c and 10d, respectively.

Following a single application of 1.25 g of E2 gel, maximum concentrations ($C_{max}$) on Day 1 were 80.2 ng/dl. On average, the time to maximum concentrations, $t_{max}$, was achieved by 20.67 H. The exposure to E1-S, as measured by AUCτ was 1359.2 ng/dl*H. Following multiple applications, Cmax concentrations increased to 163.5 ng/dl on Day 14. The $t_{max}$ estimates were approximately 5 H on Day 14 and were lower than those observed on Day 1. The exposure to E1-S was 2834.1 ng/dl*H on Day 14 and was higher than that observed on Day 1, demonstrating the accumulation of E1-S in the serum following repeated applications.

Following a single application of 2.5 g of E2 gel, maximum concentrations ($C_{max}$) on Day 1 were 74.7 ng/dl. On average, the time to maximum concentrations, $t_{max}$, was achieved by 20 H. The exposure to E1-S, as measured by AUCτ was 1207.4 ng/dl*H. Following multiple applications, Cmax concentrations increased to 253.8 ng/dl on Day 14. The $t_{max}$ estimates were approximately 3 H on Day 14 and were lower than those observed on Day 1. The exposure to E1-S was 4079.2 ng/dl*H on Day 14 and was higher than that observed on Day 1, demonstrating the accumulation of E1-S in the serum following repeated applications.

TABLE 10e

E1-Sulfate - PK Variables by Dose Regimens

| Variable | Statistic | 1.25 g Single Dose | 1.25 g Multiple Dose | 2.5 g Single Dose | 2.5 g Multiple Dose |
|---|---|---|---|---|---|
| AUC$_\tau$ [ng/dl * H] | N | 6 | 6 | 6 | 6 |
| | Mean | 1359.2 | 2834.1 | 1207.4 | 4079.2 |
| | SD | 407.8 | 1219.0 | 243.6 | 1674.5 |
| | GeoM | 1302.6 | 2611.1 | 1184.3 | 3798.7 |
| | G_CV | 33.9 | 47.2 | 22.6 | 43.4 |
| C$_{max}$ [ng/dl] | N | 6 | 6 | 6 | 6 |
| | Mean | 80.2 | 163.5 | 74.7 | 253.8 |
| | SD | 30.5 | 75.5 | 12.1 | 124.2 |
| | GeoM | 75.2 | 148.2 | 73.8 | 231.3 |
| | G_CV | 41.5 | 52.6 | 17.0 | 49.0 |
| t$_{max}$ [H] | N | 6 | 6 | 6 | 6 |
| | Mean | 20.67 | 316.67 | 20.00 | 315.33 |
| | SD | 8.16 | 3.93 | 6.20 | 4.46 |
| | Min | 4.00 | 314.00 | 12.00 | 312.00 |
| | Med | 24.00 | 315.00 | 24.00 | 313.50 |
| | Max | 24.00 | 324.00 | 24.00 | 324.00 |
| Baseline, C$_0$ [ng/dl] | N | 6 | 6 | 6 | 6 |
| | Mean | 51.3 | 51.3 | 36.9 | 36.9 |
| | SD | 17.9 | 17.9 | 10.7 | 10.7 |
| | Min | 23.3 | 23.3 | 23.3 | 23.3 |
| | Med | 55.5 | 55.5 | 38.0 | 38.0 |
| | Max | 71.0 | 71.0 | 53.0 | 53.0 |

Baseline Adjusted Estrone-Sulfate Pharmacokinetic Parameters on Day 1 and Day 14. Baseline concentrations of E1-S were similar for both groups and were measured as 51.3 ng/dl and 36.9 ng/dl for the 1.25 g and 2.5 g E2 gel, respectively. In order to correct for endogenous E1-S concentrations, the baseline E1-S concentration (E2 gel 1.25 g: 51.3 ng/dl and Bio-E-Gel 2.5 g: 36.9 ng/dl) was subtracted from the total concentration measured after application and the AUCτ and $C_{max}$ were recalculated based on the baseline-adjusted concentration. The baseline-adjusted Cmax estimates were 28.8 ng/dl and 37.7 ng/dl following single applications of the 1.25 g and 2.5 g E2 gel, respectively. For AUCτ, the baseline-adjusted values were 165.7 ng/dL*H and 325.5 ng/dl*H for the 1.25 g and 2.5 g E2 gel, respectively. Following repeated applications, $C_{max}$ estimates increased to 112.2 ng/dl and 216.9 ng/dl and AUCτ estimates increased to 1602.1 ng/dl*H and 3192.5 ng/dl*H for 1.25 g and 2.5 g E2 gel, respectively. These increases reflect the accumulation of drug in the serum following repeated application of the gel.

TABLE 10f

E1-Sulfate - PK Variables, Baseline Adjusted

| Variable | Statistic | 1.25 g Single Dose | 1.25 g Multiple Dose | 2.5 g Single Dose | 2.5 g Multiple Dose |
|---|---|---|---|---|---|
| δAUC$_τ$ [ng/dl * H] | N | 6 | 6 | 6 | 6 |
| | Mean | 165.7 | 1602.1 | 325.5 | 3192.5 |
| | SD | 63.7 | 878.6 | 267.1 | 1543.4 |
| | GeoM | 153.9 | 1403.2 | 256.1 | 2893.6 |
| | G_CV | 46.4 | 61.9 | 87.6 | 51.8 |
| δC$_{max}$ [ng/dl] | N | 6 | 6 | 6 | 6 |
| | Mean | 28.8 | 112.2 | 37.7 | 216.9 |
| | SD | 19.3 | 61.0 | 16.0 | 120.4 |
| | GeoM | 24.1 | 97.0 | 33.7 | 192.9 |
| | G_CV | 71.7 | 67.2 | 63.6 | 55.7 |

Sex Hormone Binding Globulin (SHBG). The SHBG concentrations in the subsequent table were determined in addition to the study protocol, specially in order enable the interpretation of the unexpected accumulation of E2 in Subject 04. The data are tabulated in Table 10 g. Generally the mean SHBG concentrations increased with time, after E2 gel 1.25 g from mean 72.5 nmol/l at 0 H over 80.17 nmol/l to 84.00 nmol/l and after E2 gel 2.5 g from mean 72.5 nmol/l at 0 H over 77.83 nmol/l to 88.83 nmol/l. Subject 04 who received E2 gel 2.5 g showed a similar pattern. The pre-treatment SHBG-concentrations were 58 nmol/l and 53 nmol/l, respectively. 192 H (Day 9 predose) after the first application the SHBG concentration was 58 nmol/l and after 360 H (Day 16, 0 H) it was increase to 71 nmol/l. Subject 04 thus did not appear to differ from the other subjects and the SHBG concentration do not explain the excessive E2 concentrations in this subject.

TABLE 10g

SHBG [nMol/l]

| | | Scheduled time relative to first application | | | |
|---|---|---|---|---|---|
| Treatment | Statistic | −16 | −10 | 192 | 360 |
| E2 gel, 1.25 g | N | 6 | 6 | 6 | 6 |
| | Mean | 72.33 | 72.50 | 80.17 | 84.00 |
| | SD | 23.73 | 24.83 | 28.53 | 29.18 |

TABLE 10g-continued

SHBG [nMol/l]

| | | Scheduled time relative to first application | | | |
|---|---|---|---|---|---|
| Treatment | Statistic | −16 | −10 | 192 | 360 |
| | GeoM | 69.12 | 69.02 | 75.94 | 79.73 |
| | G_CV | 34.09 | 35.54 | 37.59 | 36.85 |
| E2 gel, 2.5 g | N | 6 | 6 | 6 | 6 |
| | Mean | 74.00 | 72.50 | 77.83 | 88.83 |
| | SD | 29.64 | 30.34 | 32.17 | 38.97 |
| | GeoM | 68.91 | 67.20 | 72.20 | 81.17 |
| | G_CV | 43.88 | 45.10 | 45.01 | 50.71 |

Pharmacokinetics Conclusions. The pharmacokinetic characteristics were calculated as surrogates for the evaluation of the efficacy. It could be shown that multiple doses of 0.75 mg and 1.5 mg E2 gel resulted in average serum concentrations of about 2.4 ng/dl E2 and 5.3 ng/dl E2, respectively. These values are of a magnitude which are obtained after transdermal patches with a delivery rate of 25 and 50 μg E2 per day and are approved for postmenopausal disorders, including reduction of hot flashes.

Safety Conclusions. Eight adverse events were observed; 7 of them were classified as (possibly) related to the study treatments: 3 and 4 events after the administration of 1.25 g and 2.5 g E2 gel, respectively. Both treatments regimens showed excellent skin tolerability. No severe, serious, or significant adverse events occurred. No drop outs were observed. There were no significant changes in vital signs, ECG, clinical laboratory variables or physical findings. The study medication was well tolerated. There were no relevant differences in safety profile of the two treatments investigated.

Conclusions. The mean and individual serum concentration-time profiles for E2, E1 and E1-S from 1.25 g and 2.5 g E2 gel showed that the two treatments provided drug concentrations that were above the measured baseline levels. The pharmacokinetics of the gel product demonstrate that upon repeated administration a plateau in drug levels is generally reached. In addition, once drug is discontinued, drug levels return to or are near baseline levels within 5 days. The pharmacokinetics of E2, E1 and E1-S suggested dose proportionality for the 1.25 and 2.5 g gel products. Mean parameter estimates in the 2.5 g treatment group were approximately double the estimates in the 1.25 g treatment group on Days 1 and 14.

Estimates of $t_{max}$ were variable in both treatment groups. At steady-state on Day 14, some estimates of $t_{max}$ occurred at the beginning of the dosing interval. In these cases, it is possible that serum concentrations continued to rise immediately after a dose due to continued presence of drug from the previously administered dose. The time to maximum concentration following administration of both treatments occurred within 16–20 H after the first application.

The achievement of steady-state was assessed primarily by graphical methods. Mean trough concentrations for E2 in both treatment groups were highly variable but showed no significant increasing trend over the study period. The median trough concentration plots suggested that steady-state was reached for E2 by Day 5 in both treatment groups. Based upon the estimates of t½ for E2 obtained in this study (approximately 33 H), steady-state would be achieved after approximately 9 to 10 days of dosing, a finding which is consistent with the results of the graphical analysis. Thus, the pharmacokinetic measurements conducted on Day 14 of treatment should be representative of steady-state. Similar results were observed for E1 and E1-S although concentrations did appear to be more variable and to fluctuate more for these two analytes.

The pharmacokinetic characteristics were calculated as surrogates for the evaluation of the efficacy. It could be shown that multiple doses of 0.75 mg and 1.5 mg E2 gel resulted in average serum concentrations of about 2.4 ng/dl E2 and 5.3 ng/dl E2, respectively. These values are of a magnitude, which are obtained after transdermal patches with a delivery rate of 25 and 50 μg E2 per day and are approved for postmenopausal disorders, including reduction of hot flashes and osteoporosis. Therefore, it is predicted that E2 gel will be proven safe and effective for treatment of menopausal symptoms including reduction of hot flashes and osteoporosis.

Example 8

Study of the Safety and Efficacy of Topical E2 Gel Versus Placebo for Treatment of Vasomotor Symptoms in Postmenopausal Females. The objectives of this study were to evaluate the safety and efficacy, and determine the lowest effective dose of E2 gel, administered as a daily regimen, as compared to that of placebo gel in the treatment of vasomotor symptoms in postmenopausal women. Eligible subjects were equally randomized to one of four treatment arms: E2 gel 0.625/day (0.375 mg estradiol), E2 gel 1.25 g/day (0.75 mg estradiol), E2 gel 2.5 g/day (1.5 mg estradiol) or matching placebo gel. Eligible subjects were healthy postmenopausal women, with an estradiol level <20 pg/mL, who exhibited ≧7 moderate to severe hot flushes each day or ≧60 moderate to severe hot flushes total during 7 days of screening.

E2 gel consisted of 0.06% estradiol in a hydroalcoholic gel formulation supplied in single-dose sachets: E2 gel 0.625 g/day (0.375 mg/day E2), E2 gel 1.25 g/day (0.75 mg/day E2), or E2 gel 2.5 g/day (1.5 mg/day E2). Daily topical applications of E2 gel was administered by the subject on the thigh.

Parameters were evaluated including: hot flush occurrence rates and severity. Adverse events, safety laboratory tests, vitals signs, weight, physical examinations, breast examinations, skin irritation were assessed.

Results of the primary analyses of the co-primary efficacy endpoints indicate that the lowest effective dose of E2 gel in the treatment of vasomotor symptoms in postmenopausal women is E2 gel 2.5 g/day (1.5 mg/day E2). In the E2 gel 2.5 g/day treatment group, the difference from placebo of 2.7 in mean change from baseline in the moderate-to-severe hot flush rate at Week 4 was clinically meaningful (i.e., ≧2.0), with a complimentary superiority to placebo in mean change from baseline in daily hot flush mean severity (placebo –0.6; E2 gel 2.5 g/day, –0.9). The analogous differences from placebo in daily hot flush rate for the other E2 gel dose groups were not clinically meaningful (E2 gel 0.625 g/day, 0.7; E2 gel 1.25 g/day, 0.0).

TABLE 11

Daily Moderate-to-Severe Hot Flush Rates: Mean Change from Baseline[a]

| Evaluation | Placebo (N = 42) | E2 Gel 0.625 g/day (N = 41) | E2 Gel 1.25 g/day (N = 39) | E2 Gel 2.5 g/day (N = 38) |
|---|---|---|---|---|
| Baseline (Mean ± SD)[b] | 16.0 ± 9.88 | 12.5 ± 5.60 | 12.3 ± 7.26 | 13.0 ± 5.97 |
| Week –1 (Placebo Lead-In) | –5.3 | –3.9 | –4.7 | –5.0 |
| Week 1 | –7.3 | –5.8 | –5.9 | –7.5 |
| Week 2 | –7.9 | –7.5 | –7.2 | –9.4 |
| Week 3 | –8.5 | –8.5 | –7.4 | –10.5 |
| Week 4 | –8.5 | –9.2 | –8.5 | –11.2 |

[a]For Week –1 through Week 4, means are least squares means derived from the ANCOVA model with factors for treatment, site, and treatment-by-site interaction, with baseline hot flush rate as the covariate.
[b]Unadjusted means and standard deviations. Baseline based on the first 7 days of the Screening Period.

As in the primary efficacy analyses, comparison of treatment groups with respect to the proportion of subjects with a ≧90% reduction in daily moderate-to-severe hot flush rate at Week 4 indicates effectiveness in the E2 gel 2.5 g/day group (55% of subjects), while the other E2 gel dose groups performed similar to placebo (27% to 35%). Furthermore, the median estradiol concentration at Week 4 for the E2 gel 2.5 g/day dose group (33 pg/mL) is in the low end of the expected therapeutic range, with the median concentrations falling below the range for the other E2 gel dose groups (E2 gel 0.625 g/day, 12 pg/mL; E2 gel 1.25 g/day, 23 pg/mL).

Analyses of Efficacy. The primary efficacy evaluation of the clinical effectiveness of E2 gel 0.625 g/day (0.375 mg E2), E2 gel 1.25 g/day (0.75 mg E2), and E2 gel 2.5 g/day (1.5 mg E2) as compared to placebo was determined with respect to change from baseline in daily (moderate-to-severe) hot flush rate at Week 4 and change from baseline in daily hot flush mean severity at Week 4 evaluated in the ITT LOCF Data Set. The baseline measures used in these analyses are based on data obtained during the Screening Period analyses with baseline measures based on data obtained during the Placebo Lead In Period were not included.

The primary analysis of change from baseline in daily hot flush mean severity was based on unadjusted means from the one-way ANOVA model with treatment as the factor. However, in consideration of dissimilarity across treatment groups with respect to mean baseline daily hot flush rates, as well as an apparent treatment-by-site interaction, the primary analysis of change from baseline in daily hot flush rate was based on least-squares means derived from the ANCOVA model with factors for treatment, site, and treatment-by-site interaction, with baseline hot flush rate as the covariate. Only these primary analysis results are discussed.

As secondary efficacy analyses, the analyses of the 2 co-primary endpoints described above were performed on the Evaluable Subject LOCF Data Set. Additional analyses included the proportions of subjects who had a ≧50%, ≧60%, ≧70%, ≧80%, ≧90%, ≧95% or 100% reduction from baseline in daily moderate-to-severe hot flush rate at Week 4, conducted for the ITT LOCF and the Evaluable Subject LOCF Data Sets. For the ITT Data Set, the results of these proportion analyses are presented in a text table.

Descriptive analyses of the 2 co-primary endpoints were performed for the ITT Observed-Case Data Set and the Evaluable Subject Observed-Case Data Set at Week 1, Week 2, Week 3, and Week 4. Since only 4 subjects discontinued treatment prematurely, the results of the observed-case analyses on these data sets are nearly identical to those from the LOCF analyses and are therefore not discussed explicitly in this report.

Mean Change from Baseline in Daily Moderate-to-Severe Hot Flush Rates. Intent-to-Treat Data Set—LOCF Analyses. In the LOCF analyses of the ITT Data Set, mean reductions from baseline in daily moderate-to-severe hot flush rates were observed for all four treatment groups, with a more pronounced reduction observed in the E2 gel 2.5 g/day dose group (see Table 11a and FIG. 5a).

A clinically significant difference (i.e., $\geq 2.0$) was observed between the E2 gel 2.5 g/day group and placebo in the mean reduction of daily hot flush rate at Week 4 (difference between groups=−2.7), while the two lower doses of E2 gel did not show a clinically meaningful difference from placebo. Therefore, the two lower E2 gel doses are non-effective and the E2 gel 2.5 g/day dose is demonstrated to be the lowest effective dose for the treatment of moderate-to-severe hot flushes.

Figure 5A:
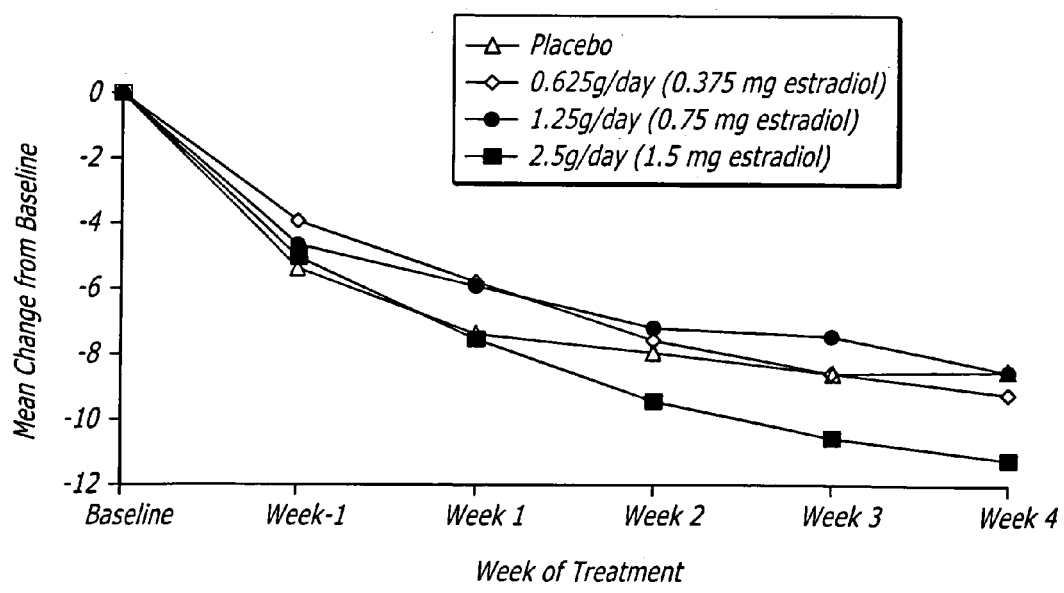
FIG. 5A is a graph depicting mean change from baseline in daily moderate-to-severe hot flush rate after E2+0% LA gel at various doses (Intent-to-treat efficacy population ("ITT"); Method of last observation carried forward for subjects who discontinued early ("LOCF").

FIG. 5A is a graph depicting mean change from baseline in daily moderate-to-severe hot flush rate after estradiol at various doses (ITT-LOCF).

TABLE 11a

Mean Change from Baseline in Daily Moderate-to-Severe Hot Flush Rate (ITT-LOCF)

| | Mean Change from Baseline | | | |
|---|---|---|---|---|
| Evaluation | Placebo (N = 42) | E2 Gel 0.625 g/day (N = 41) | E2 Gel 1.25 g/day (N = 39)[b] | E2 Gel 2.5 g/day (N = 38)[c] |
| Baseline (Mean ± SD)[d] | 16.0 ± 9.88 | 12.5 ± 5.60 | 12.3 ± 7.26 | 13.0 ± 5.97 |
| Week −1 (Placebo Lead-In) | −5.3 | −3.9 | −4.7 | −5.0 |
| Week 1 | −7.3 | −5.8 | −5.9 | −7.5 |
| Week 2 | −7.9 | −7.5 | −7.2 | −9.4 |
| Week 3 | −8.5 | −8.5 | −7.4 | −10.5 |
| Week 4 | −8.5 | −9.2 | −8.5 | −11.2 |

[a]For Week −1 through Week 4, means are least squares means derived from the ANCOVA model with factors for treatment, site, and treatment-by-site interaction, with baseline hot flush rate as the covariate.
[b]Though 40 subjects are in the ITT Bio-E-Gel 1.25 g/day treatment group, Subject 102 is not included in the hot flush analyses due to intractable baseline data.
[c]For the evaluation at Week 1, N = 37 for the E2 gel 2.5 g/day treatment group since the hot flush diary for Subject 187 for that week was lost.
[d]Unadjusted means and standard deviations. Baseline based on the first 7 days of the Screening Period.

Evaluable Subject Dataset—LOCF Analyses. In the LOCF analyses of the Evaluable Subject Data Set, mean reductions from baseline in daily moderate-to-severe hot flush rates were observed for all 4 treatment groups, with a more pronounced reduction observed in the E2 gel 2.5 g/day dose group (see Table 11b and FIG. 5b). A clinically significant difference (i.e., $\geq 2.0$) was observed between the E2 gel 2.5 g/day dose group and placebo in the mean reduction of daily hot flush rate at Week 4 (difference between groups=−3.2), while the two lower doses of E2 gel did not show a clinically meaningful difference from placebo.

Figure 5B:
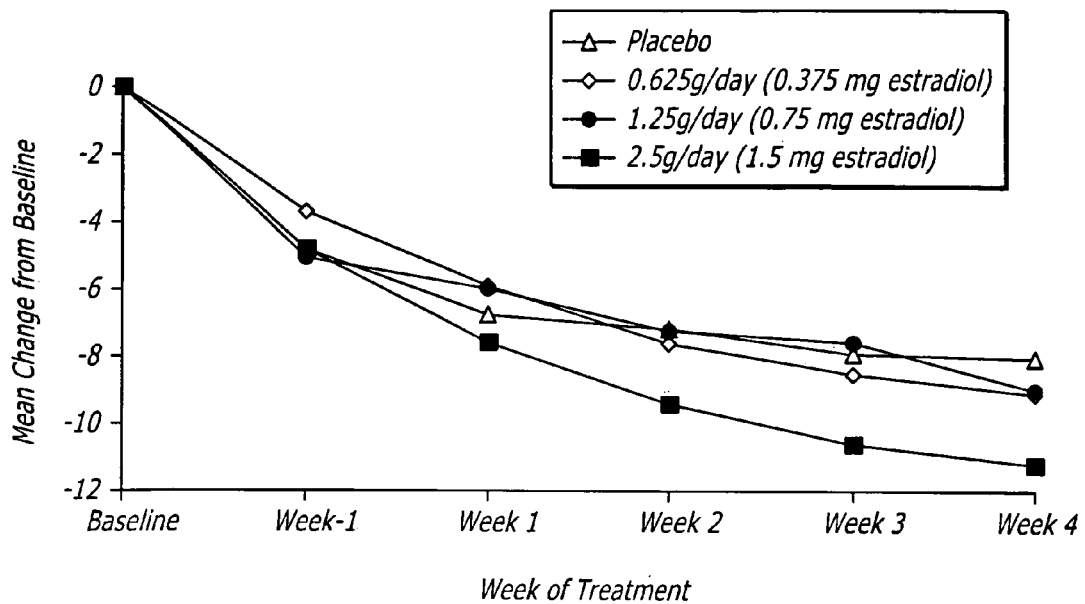
FIG. 5B is a graph depicting mean change from baseline in daily moderate-to-severe hot flush rate after E2+0% LA gel at various doses (Evaluable-LOCF).

FIG. 5B is a graph depicting mean change from baseline in daily moderate-to-severe hot flush rate after estradiol at various doses (Evaluable-LOCF).

TABLE 11b

Mean Change from Baseline in Daily Moderate-to-Severe Hot Flush Rate (Evaluable-LOCF)

| | Mean Change from Baseline[a] | | | |
|---|---|---|---|---|
| Evaluation | Placebo (N = 28) | E2 Gel 0.625 g/day (N = 38) | E2 Gel 1.25 g/day (N = 33) | E2 Gel 2.5 g/day (N = 30) |
| Baseline (Mean ± SD)[b] | 15.3 ± 9.35 | 12.3 ± 5.11 | 12.8 ± 7.73 | 13.4 ± 5.91 |
| Week −1 (Placebo Lead-In) | −4.8 | −3.7 | −5.0 | −4.8 |
| Week 1 | −6.7 | −5.9 | −6.0 | −7.6 |
| Week 2 | −7.1 | −7.6 | −7.3 | −9.4 |
| Week 3 | −7.9 | −8.5 | −7.6 | −10.6 |
| Week 4 | −8.0 | −9.1 | −9.0 | −11.2 |

[a]For Week −1 through Week 4, means are least squares means derived from the ANCOVA model with factors for treatment, site, and treatment-by-site interaction, with baseline hot flush rate as the covariate.
[b]Unadjusted means and standard deviations. Baseline based on the first 7 days of the Screening Period.

Proportion of Subjects with $\geq 90\%$ or 100% Percent Reductions in Daily Moderate-to-Severe Hot Flush Rates at Week 4. Intent-to-Treat Data Set—LOCF Analyses. In the LOCF analyses of the ITT Data Set, the majority (55%, 21/38) of subjects in the E2 gel 2.5 g/day dose group experienced a $\geq 90\%$ reduction in daily moderate-to-severe hot flush rate at Week 4, compared to approximately a third of subjects in placebo and the two lower E2 gel dose groups (see Table 11c). Twenty-four percent (24%) of subjects in the E2 gel 2.5 g/day dose group had a 100% reduction (i.e., no moderate-to-severe hot flushes) at Week 4.

TABLE 11c

Number and Proportion of Subjects with a $\geq 50\%$ to a 100% Reduction in Daily Moderate-to-Severe Hot Flush Rates at Week 4 (ITT-LOCF)

| | Number (%) of Subjects | | | |
|---|---|---|---|---|
| Evaluation | Placebo (N = 42) | E2 Gel 0.625 g/day (N = 41) | E2 Gel 1.25 g/day (N = 39)[a] | E2 Gel 2.5 g/day (N = 38) |
| $\geq 50\%$ Reduction | 32 (76%) | 31 (76%) | 32 (82%) | 33 (87%) |
| $\geq 60\%$ Reduction | 29 (69%) | 29 (71%) | 28 (72%) | 32 (84%) |
| $\geq 70\%$ Reduction | 24 (57%) | 21 (51%) | 23 (59%) | 29 (76%) |
| $\geq 80\%$ Reduction | 19 (45%) | 15 (37%) | 17 (44%) | 24 (63%) |
| $\geq 90\%$ Reduction | 13 (31%) | 11 (27%) | 14 (36%) | 21 (55%) |
| $\geq 95\%$ Reduction | 8 (19%) | 7 (17%) | 12 (31%) | 19 (50%) |
| 100% Reduction | 4 (10%) | 4 (10%) | 8 (21%) | 9 (24%) |

[a]Though 40 subjects are in the ITT E2 Gel 1.25 g/day treatment group, Subject 102 is not included in the hot flush analyses due to intractable baseline data.

Mean Change from Baseline Severity of Hot Flushes. Intent-to-Treat Data Set—LOCF Analyses. In the LOCF analyses of the ITT Data Set, mean reductions from baseline daily hot flush mean severity were observed for all four treatment groups, with a more pronounced reduction observed in the E2 gel 2.5 g/day dose group, and to a lesser degree, in the E2 gel 1.25 g/day dose group (see Table 11d and FIG. 5c). The decrease in daily hot flush mean severity over time in the E2 gel 2.5 g/day dose group is complimentary to the clinically meaningful difference from placebo seen at Week 4 in mean reduction of daily hot flush rate.

Figure 5C:
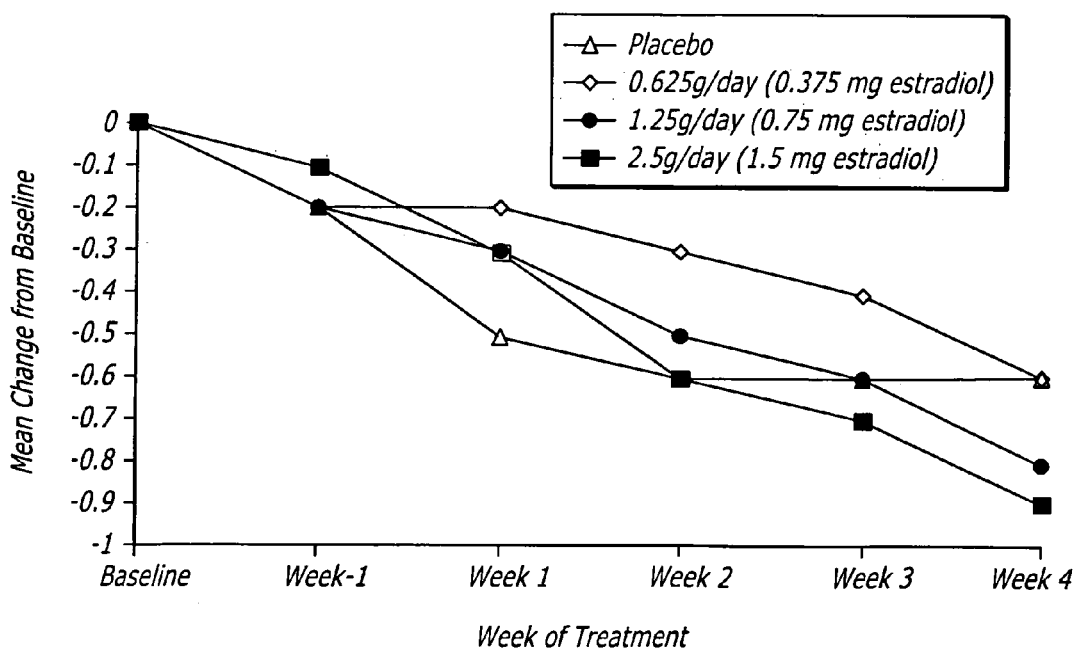
FIG. 5C is a graph depicting mean change from baseline in daily hot flush mean severity after E2+0% LA gel at various doses (ITT-LOCF).

FIG. 5C is a graph depicting mean change from baseline in daily hot flush mean severity after estradiol at various doses (ITT-LOCF).

TABLE 11d

Mean Change from Baseline in Daily Hot Flush Mean Severity (ITT-LOCF)

| Evaluation | Mean Change from Baseline[a] | | | |
|---|---|---|---|---|
| | Placebo (N = 42) | E2 Gel 0.625 g/day (N = 41) | E2 Gel 1.25 g/day (N = 39)[b] | E2 Gel 2.5 g/day (N = 38)[c] |
| Baseline (Mean ± SD)[d] | 2.3 ± 0.31 | 2.2 ± 0.30 | 2.3 ± 0.33 | 2.2 ± 0.33 |
| Week −1 (Placebo Lead-In) | −0.2 | −0.2 | −0.2 | −0.1 |
| Week 1 | −0.5 | −0.2 | −0.3 | −0.3 |
| Week 2 | −0.6 | −0.3 | −0.5 | −0.6 |
| Week 3 | −0.6 | −0.4 | −0.6 | −0.7 |
| Week 4 | −0.6 | −0.6 | −0.8 | −0.9 |

[a]Severity scale: 1 = mild, 2 = moderate, 3 = severe.
[b]Though 40 subjects are in the ITT Bio-E-Gel 1.25 g/day treatment group, Subject 102 is not included in the hot flush analyses due to intractable baseline data.
[c]For the evaluation at Week 1, N = 37 for the Bio-E-Gel 2.5 g/day treatment group since the hot flush diary for Subject 187 for that week was lost.
[d]Unadjusted means and standard deviations. Baseline based on the first 7 days of the Screening Period.

Drug Dose, Drug Concentration, and Relationships to Response. Estradiol, Estrone, and Estrone Sulfate. Trough serum samples were obtained prior to dosing on Day 1 and upon study completion for determination of estradiol, estrone, and estrone sulfate concentrations. For summarization, all assay results below the detection limit of 5 pg/mL were set equal to the limit (i.e., assigned a value of 5 pg/mL). Trough concentrations of estradiol, estrone, and estrone sulfate at Day 1 and Week 4 were highly variable within treatment groups (see Table 11e). In consideration of the variability and the moderate sample sizes, median values will be discussed.

Across all treatment groups, median values at Day 1 for estradiol (5 pg/mL), estrone (18.5 to 22.0 pg/mL), and the estradiol-to-estrone ratio (0.29 to 0.42) were consistent with a postmenopausal profile (see Table 11e). However, note that some subjects who met the inclusion criterion of <20 pg/mL estradiol at screening failed to meet this criterion at Day 1. Apart from variability inherent to the assay, speculative reasons for this are instability of hormone levels for subjects with menopause onset within the prior year, hysterectomy without oophorectomy in subjects <50 years of age, or possible unreported noncompliance regarding use of an estrogen product during the Screening Period.

After therapy with E2 gel, median estradiol, estrone, and estrone sulfate concentrations at Week 4 showed separation between treatment groups in accord with E2 gel dose administration (see Table 11e). The median estradiol values at Week 4 were 12 pg/mL, 23 pg/mL, and 33 pg/mL, respectively, for the E2 gel 0.625 g/day, 1.25 g/day, and 2.5 g/day dose groups.

TABLE 11e

Trough Estradiol, Estrone, and Estrone Sulfate at Day 1 and Week 4 (ITT)

| Hormone | Evaluation | Placebo | E2 Gel 0.625 g/day | E2 Gel 1.25 g/day | E2 Gel 2.5 g/day |
|---|---|---|---|---|---|
| E2 (pg/mL) | Day 1 | (N = 41) | (N = 41) | (N = 39) | (N = 38) |
| | Mean ± SD | 12.2 ± 18.5 | 15.3 ± 24.5 | 10.3 ± 13.5 | 12.3 ± 20.3 |
| | Median | 5 | 5 | 5 | 5 |
| | Range | 5–110 | 5–120 | 5–64 | 5–110 |
| | Week 4 | (N = 40) | (N = 41) | (N = 37) | (N = 37) |
| | Mean ± SD | 11.4 ± 15.4 | 24.1 ± 41.6 | 34.8 ± 33.0 | 46.8 ± 44.6 |
| | Median | 5 | 12 | 23 | 33 |
| | Range | 5–85 | 5–240 | 5–170 | 5–250 |
| E1 (pg/mL) | Day 1 | (N = 41) | (N = 41) | (N = 39) | (N = 38) |
| | Mean ± SD | 22.3 ± 13.9 | 29.9 ± 28.1 | 24.3 ± 15.8 | 22.4 ± 13.9 |
| | Median | 19.0 | 22.0 | 22.0 | 18.5 |
| | Range | 5–65 | 6–160 | 5–93 | 5–67 |
| | Week 4 | (N = 40) | (N = 41) | (N = 37) | (N = 36) |
| | Mean ± SD | 21.6 ± 15.3 | 36.3 ± 15.7 | 51.9 ± 29.1 | 72.3 ± 43.8 |
| | Median | 19.5 | 35.0 | 44.0 | 60.5 |
| | Range | 5–82 | 5–78 | 13–130 | 17–200 |
| E2/E1 Ratio | Day 1 | (N = 41) | (N = 41) | (N = 39) | (N = 38) |
| | Mean ± SD | 0.55 ± 0.52 | 0.49 ± 0.36 | 0.43 ± 0.29 | 0.47 ± 0.33 |
| | Median | 0.42 | 0.31 | 0.29 | 0.39 |
| | Range | 0.2–2.9 | 0.0–1.6 | 0.1–1.2 | 0.2–2.0 |
| | Week 4 | (N = 40) | (N = 41) | (N = 37) | (N = 36) |
| | Mean ± SD | 0.59 ± 0.59 | 0.55 ± 0.56 | 0.67 ± 0.59 | 0.64 ± 0.33 |
| | Median | 0.37 | 0.35 | 0.51 | 0.54 |
| | Range | 0.2–3.2 | 0.2–3.3 | 0.2–3.8 | 0.2–1.7 |
| E1-S (pg/mL) | Day 1 | (N = 41) | (N = 41) | (N = 39) | (N = 38) |
| | Mean ± SD | 532.4 ± 350.2 | 691.0 ± 815.5 | 457.4 ± 193.9 | 523.2 ± 443.5 |
| | Median | 410.0 | 480.0 | 430 | 430.0 |
| | Range | 150–2100 | 170–4760 | 190–940 | 180–2650 |

TABLE 11e-continued

Trough Estradiol, Estrone, and Estrone Sulfate at Day 1 and Week 4 (ITT)

| Hormone | Evaluation | Placebo | E2 Gel 0.625 g/day | E2 Gel 1.25 g/day | E2 Gel 2.5 g/day |
|---|---|---|---|---|---|
| | Week 4 | (N = 40) | (N = 40) | (N = 38) | (N = 36) |
| | Mean ± SD | 573 ± 616.6 | 944.4 ± 579.1 | 1562 ± 1610 | 2283 ± 1884 |
| | Median | 400.0 | 740.0 | 995.0 | 1765 |
| | Range | 110–4020 | 300–2870 | 280–8020 | 330–7040 |

Safety Conclusions. Daily application of 0.625–2.5 g E2 gel (0.375–1.5 mg estradiol) for approximately 4 weeks was safe and well-tolerated in this population of postmenopausal females. The overall incidence of treatment-emergent adverse events among the E2 gel groups was not increased with dose level (approximately 50% in each dose group), and compared well to the incidence in the placebo group (40%). Adverse events associated with reproductive system and breast disorders were reported more frequently in the E2 gel groups (10%, 18%, and 13% in the 0.625 g/day, 1.25 g/day, and 2.5 g/day E2 gel groups, respectively) versus placebo (5%), as would be expected in this class of drugs. These events reported in 2 or more E2 gel subjects included: breast tenderness, metrorrhagia (vaginal spotting), nipple pain, uterine spasm, and vaginal discharge. No relationship was apparent between the incidence of these events and E2 gel dose or estradiol level. No subjects discontinued the study due to these events.

Breast examination indicated no effect of E2 gel at final evaluation for all but one subject; the change observed for this subject (E2 gel 2.5 g/day) corresponded to one of the reported adverse events of mild breast tenderness, which resolved one week after final study drug administration.

No deaths or serious adverse events occurred during the study. Two (2) subjects (both E2 gel 1.25 g/day) discontinued double-blind treatment due to an adverse event, only one of which (dizziness) was considered possibly related; both subjects recovered.

No clinically meaningful effects of E2 gel on clinical laboratory results were observed in analyses of mean change from baseline to Week 4 evaluations. Comparisons of proportions of subjects with shifts from normal baselines to abnormal levels at Week 4 indicated a higher incidence of shifts to above normal cholesterol levels in E2 gel groups, and an apparent E2 gel dose-related increased incidence of shifts to above normal BUN levels; however, only about 10 subjects per group were included in the cholesterol comparison (since most subjects had above normal baseline cholesterol levels), and the BUN shifts were not associated with corresponding shifts in other renal function indicators or clinical manifestations of renal insufficiency.

No clinically important effects of E2 gel were observed for vital signs, body weight, physical examinations, or skin irritation assessment.

Conclusion. Transdermal ET delivers estradiol directly into the systemic circulation via the skin, thus avoiding the first-pass hepatic metabolism that occurs with oral ET and avoiding the effects on the hepatobiliary system seen with oral ET. No statistically significant or clinically meaningful changes noted in the mean change from baseline to Week 4 evaluation were observed for any liver function parameters. One subject in the E2 gel 0.625 g/day dose group experienced an increased AST that the investigator felt was clinically significant; also this subject had an elevated ALT (44 u/L) at baseline that increased to 70 u/L at final evaluation. No subjects were observed to have clinically significant increases in liver function tests in the E2 gel 1.25 g/day or E2 gel 2.5 g/day dose groups.

Adverse events associated with the topical application of the study gel were minimal and were more frequently reported in the E2 gel 1.25 g/day dose group. Dry skin at the application site was the most frequently reported event associated with the application of study drug, occurring in two subjects. These events were considered mild, with the onset greater than 2 weeks on study drug, and the events lasted no longer than 7 days. Other skin related events reported included burning or itching at the application site, occurring in one subject for each event. No treatment-emergent erythema at application site occurred.

Oral ET has been shown to produce an increase in the biliary cholesterol saturation index, and is associated with an increased risk of gallstones disease; however, this effect does not appear to be evident in transdermal ET. No subjects in the E2 gel dose groups were noted to have clinically significant changes in bilirubin levels, and no adverse events related to increased cholesterol, bilirubinemia, or gallstones were reported.

While it was initially thought that the use of transdermal ET would avoid the increases in serum lipids and lipoproteins seen with oral ET, studies have shown that changes in serum lipids and lipoproteins do occur, but with onset and progression that is slower than with oral ET. In this 4 week study, clinically meaningful mean changes were not observed in these parameters, though overall changes would not be expected in just a 4-week duration of treatment. One subject in the E2 gel 2.5 g/day dose group had a clinically significant change from baseline in triglycerides; however, the subject's final laboratory blood draw was non-fasting. Incidentally, this subject's baseline cholesterol was 287 mg/dL and LDL was 172 mg/dL.

The results of this study demonstrate that E2 gel administered daily in doses of 0.625–2.5 g/day for 4 weeks is safe and well-tolerated.

The particular embodiments of the invention having been described above are not limiting of the present invention, and those of skill in the art can readily determine that additional embodiments and features of the invention are within the scope of the appended claims and equivalents thereto.

While the specification describes particular embodiments of the present invention, those of ordinary skill can devise variations of the present invention without departing from the inventive concept. Thus, the invention described and claimed herein is not to be limited in scope by the specific embodiments disclosed herein, since these embodiments are intended as illustrations of several aspects of the invention.

Any equivalent embodiments are intended to be within the scope of the invention. Indeed, various modifications of the invention in addition to those shown and described herein will become apparent to those skilled in the art from the foregoing description. Such modifications are also intended to fall within the scope of the appended claims.

What is claimed is:

1. A formulation for transdermal or transmucosal administration of an active agent, the formulation comprising: at least one active agent, provided that when the active agent is estrogen, a progestin is not present in the formulation, and when the active agent is progestin, estrogen is not present in the formulation; and a delivery vehicle comprising a $C_2$ to $C_4$ alkanol, a polyalcohol, and a permeation enhancer of monoalkyl ether of diethylene glycol present in an amount sufficient to provide permeation enhancement of the active agent through dermal or mucosal surfaces; wherein the formulation is substantially free of long-chain fatty alcohols, long-chain fatty acids, and long-chain fatty esters in order to avoid undesirable odor and irritation effects caused by such compounds during use of the formulation.

2. The formulation of claim 1, wherein the polyalcohol is present in an amount between about 1% and 30% of the vehicle; and the permeation enhancer is present in an amount of between about 0.2% and 25% of the vehicle.

3. The formulation of claim 1, wherein the active agent is testosterone present in an amount between about 0.05% to 10% of the formulation; the alkanol is present in an amount between about 20 to 65% of the formulation; the polyalcohol is propylene glycol present in an amount between about 1% to 15% of the formulation; the permeation enhancer is diethylene glycol monoethyl ether present in an amount between about 1% to 15% of the formulation, and further wherein the formulation comprises a gelling agent present in an amount of between 0.05% to about 4% of the formulation, a neutralizing agent present in an amount between about 0.05% and 1% of the formulation, and water present in an amount between about 20% to 65% of the formulation.

4. The formulation of claim 3, wherein the formulation further includes a sequestering agent.

5. The formulation of claim 1, wherein the polyalcohol and permeation enhancer are present in a weight ratio of 2:1 to 1:1.

6. The formulation of claim 1, wherein the polyalcohol and permeation enhancer are present in a weight ratio of 1.25:1 to 1.2:1.

7. The formulation of claim 1, wherein the alkanol is present in an amount of 5 to 75% by weight of the vehicle.

8. The formulation of claim 1, wherein the alkanol is selected from the group consisting of ethanol, isopropanol and n-propanol.

9. The formulation of claim 1, wherein the polyalcohol is polypropylene glycol.

10. The formulation of claim 1 wherein the active agent is selected from the group including androgens, estrogens, or progestogens or any combination thereof.

11. The formulation of claim 1, wherein the active agent is selected from the group consisting of androgens, anti-androgens, estrogens, anti-estrogens, progestogens, anti-progestogens, adrenergic agonists, analgesics, sedatives, amides, arylpiperazines, nerve agents, antineoplastics, anti-inflammatory agents, anticholinergics, anticonvulsants, antidepressants, antiepileptics, antihistaminics, antihypertensives, muscle relaxants, diuretics, bronchodilators, and glucocorticoids.

12. The formulation of claim 1, wherein the at least one active agent is in combination with a secondary active agent for concurrent administration.

13. The formulation of claim 12, wherein the at least one or secondary active agent is a combination of methyltestosterone and esterified estrogen.

14. The formulation of claim 12, wherein the at least one or secondary active agent is a combination of testosterone and nandrolone decanoate.

15. The formulation of claim 12, wherein the at least one or secondary active agent is a combination of testosterone and estradiol.

16. The formulation of claim 1, wherein the formulation further comprises at least one of a gelling agent, neutralizing agent, sequestering agent, buffering agent, moisturizing agent, humectant, surfactant, antioxidant, emollient, or buffer.

17. The formulation of claim 16, wherein the gelling agent is selected from the group consisting of carbomer, carboxyethylene, polyacrylic acid, cellulose derivatives, ethylcellulose, hydroxypropylmethylcellulose, ethylhydrooxyethylcellulose, carboxymethylcellulose, hydroxypropylcellulose, hydroxyethylcellulose, natural gums, arabic, xanthan, guar gums, alginates, polyvinylpyrrolidone derivatives, polyoxyethylene polyoxypropylene copolymers, chitosan, polyvinyl alcohol, pectin, and veegum.

18. The formulation of claim 16, wherein the buffering agent is selected from the group consisting of carbonate buffers, citrate buffers, phosphate buffers, acetate buffers, hydrochloric acid, lactic acid, tartric acid, diethylamine, triethylamine, diisopropylamine, tetrahydroxypropylethylendiamine, and aminomethylamine.

19. The formulation of claim 16, wherein the sequestering agent is edetic acid.

20. The formulation of claim 1 wherein the formulation is in the form of a gel, lotion, cream, spray, aerosol, ointment, emulsion, suspension, liposomal system, lacquer, patch, bandage, or occlusive dressing.

21. A formulation for transdermal or transmucosal administration of an active agent, the formulation comprising: at least one active agent, provided that when the active agent is estrogen, a progestin is not present in the formulation, and when the active agent is progestin, estrogen is not present in the formulation; and a delivery vehicle comprising a $C_2$ to $C_4$ alkanol, a polyalcohol, and a permeation enhancer of monoalkyl ether of diethylene glycol to provide permeation enhancement of the active agent through dermal or mucosal surfaces, wherein the polyalcohol is propylene glycol and is present in an amount between about 1% and 30% of the vehicle, the permeation enhancer is diethylene glycol monoethyl ether and is present in an amount of between about 0.2% and 25% of the vehicle, the alkanol is ethanol and is present in an amount of 5 to 75% by weight of the vehicle wherein the formulation is substantially free of long-chain fatty alcohols, long-chain fatty acids, and long-chain fatty in order to avoid undesirable odor and irritation effects caused by such compounds during use of the formulation.

22. The formulation of claim 21, wherein the polyalcohol and permeation enhancer are present in a weight ratio of 2:1 to 1:1.

23. The formulation of claim 1 wherein the formulation comprises at least one of a gelling agent, neutralizing agent, sequestering agent, buffering agent, moisturizing agent, humectant, surfactant, antioxidant, emollient, or buffer and is in the form of a gel, lotion, cream, spray, aerosol, ointment, emulsion, suspension, liposomal system, lacquer, patch, bandage, or occlusive dressing.

24. A formulation for epithelial administration of an active agent, the formulation comprising: at least one active agent comprising an androgen; and a delivery vehicle comprising a $C_2$ to $C_4$ alkanol, a polyalcohol, and a permeation enhancer of monoalkyl ether of diethylene glycol present in an amount sufficient to provide permeation enhancement of the active agent through epidermal surfaces; wherein the formulation is substantially free of long-chain fatty alcohols, long-chain fatty acids, and long-chain fatty esters in order to avoid undesirable odor and irritation effects caused by such compounds during use of the formulation.

25. The formulation of claim 24, wherein the alkanol is ethanol, the polyalcohol is propylene glycol, and the permeation enhancer is monoethyl ether of diethylene glycol.

26. The formulation of claim 24, wherein the formulation is in the form of a gel.

27. The formulation of claim 24, wherein the active agent is a combination of testosterone with estrogen or progestin.

28. The formulation of claim 1, wherein the active agent is estrogen or progestin.

* * * * *

UNITED STATES PATENT AND TRADEMARK OFFICE
CERTIFICATE OF CORRECTION

| | | |
|---|---|---|
| PATENT NO. | : 7,198,801 B2 | Page 1 of 1 |
| APPLICATION NO. | : 10/798161 | |
| DATED | : April 3, 2007 | |
| INVENTOR(S) | : Carrara et al. | |

It is certified that error appears in the above-identified patent and that said Letters Patent is hereby corrected as shown below:

<u>Title Page</u>:
Item (63), "Related Application Data", after "Aug. 3, 2001", delete ", said application No. 10/798,161".

<u>Column 34</u>:
Line 55 (claim 21, line 17), after "fatty alcohols, long-chain fatty acids, and long-chain fatty", insert -- esters --.

Signed and Sealed this

Nineteenth Day of June, 2007

JON W. DUDAS
*Director of the United States Patent and Trademark Office*